(12) United States Patent
Cheatham et al.

(10) Patent No.: US 7,943,572 B2
(45) Date of Patent: May 17, 2011

(54) SUPERIOR CONTROL OF BLOOD GLUCOSE IN DIABETES TREATMENT

(75) Inventors: Wayman Wendell Cheatham, Columbia, MD (US); Anders Hasager Boss, Princeton, NJ (US)

(73) Assignee: MannKind Corporation, Valencia, CA (US)

( * ) Notice: Subject to any disclaimer, the term of this patent is extended or adjusted under 35 U.S.C. 154(b) by 212 days.

(21) Appl. No.: 11/278,381

(22) Filed: Mar. 31, 2006

(65) Prior Publication Data
US 2006/0239934 A1 Oct. 26, 2006

Related U.S. Application Data

(63) Continuation-in-part of application No. 11/329,686, filed on Jan. 10, 2006.

(60) Provisional application No. 60/667,393, filed on Mar. 31, 2005.

(51) Int. Cl.
*A61K 38/28* (2006.01)
(52) U.S. Cl. ......................................................... 514/5.9
(58) Field of Classification Search ......................... None
See application file for complete search history.

(56) References Cited

U.S. PATENT DOCUMENTS

| | | | |
|---|---|---|---|
| 5,352,461 A | 10/1994 | Feldstein et al. | |
| 5,503,852 A | 4/1996 | Steiner et al. | |
| 5,506,203 A | 4/1996 | Backstrom et al. | |
| 5,547,929 A | 8/1996 | Anderson, Jr. et al. | |
| 5,888,477 A | 3/1999 | Gonda et al. | |
| 5,976,569 A | 11/1999 | Milstein | |
| 6,071,497 A | 6/2000 | Steiner et al. | |
| 6,331,318 B1 | 12/2001 | Milstein | |
| 6,395,774 B1 | 5/2002 | Milstein | |
| 6,428,771 B1 | 8/2002 | Steiner et al. | |
| 6,444,226 B1 | 9/2002 | Steiner et al. | |
| 6,652,885 B2 * | 11/2003 | Steiner et al. | 424/489 |
| 6,923,175 B2 | 8/2005 | Poole et al. | |
| 2004/0062722 A1 | 4/2004 | Gonda et al. | |
| 2004/0182387 A1 | 9/2004 | Steiner et al. | |
| 2005/0153874 A1 * | 7/2005 | Cheatham et al. | 514/3 |
| 2006/0040953 A1 | 2/2006 | Leone-Bay et al. | |
| 2006/0153778 A1 * | 7/2006 | Gelber et al. | 424/46 |
| 2007/0020191 A1 * | 1/2007 | Boss et al. | 424/45 |

FOREIGN PATENT DOCUMENTS

| | | |
|---|---|---|
| EP | 0220958 | 5/1987 |
| WO | 96/36314 | 11/1996 |
| WO | 99/52506 | 10/1999 |
| WO | WO 01/00654 | * 1/2001 |

OTHER PUBLICATIONS

Cefalu et al. "Inhaled Human Insulin Treatment in Patients with Type 2 Diabetes Mellitus," Ann. Int. Med., 2001, 134, 203-7.*

Nathan, D.M. et al. "Intensive diabetes treatment and cardiovascular disease in patients with Type 1 diabetes." New Eng. J. Med. 353:2643-3653, 2005.
Cefalu WT., "Concept, strategies and feasibility of noninvasive insulin delivery", Diabetes Care 27:239-246, 200.
Cerasi, et al., "Decreased sensitivity of the pancreatic beta cells to glucose in prediabetic and diabetic subjects. A glucose dose-response study", Diabetes 21(4):224-34, 1974.
Gupta et al., "Contemporary approaches in aerosolized drug delivery to the lung", J. controlled Research, 17:129-148, 1991.
Heinemann, et al., "Current status of the development of inhales insulin", Br J Diabetes Vasc Dis, 4:295-301, 2004d.
Leahy, et al., "Beta-ell dysfunction in type II diabetes mellitus", Curr Opin Endocrinol Diabetes, 2:300-306, 1995.
Lian, et al., "A self-complementary self-assembling microsphere system: application for intravenous delivery of the antiepileptic and neuroprotectant compound felbanate", J. Pharm Sci 89:867-875, 2000.
Pfeifer MA, et al., "Insulin secretion in diabetes mellitus", Am J Med, 70:579-88, 1981.
Polonsky, et al., "Abnormal patterns of insulin secretion in non-insulin-dependent diabetes mellitus", N Eng J Med, 318:1231-39, 1988.
Steiner, S. et al., "Technosphere (TM) /Insulin—proof of concept study with a new insulin formulation for pulmunary delivery", Exp Clin Endocrinol Diabetes, 110:17-21, 2002.
Edelman, SV., "Type II diabetes mellitus", Adv Int Med, 43:449-500, 1998.
Kohler, D., et al., "Non-radioactive approach for measuring lung permeability: inhalation of insulin", Atemw Lungenkrkh, 13:230-232, 1987 (Original German and English translation attached).
Raz, et al., "Pharmacodynamics and pharmacokinetics of dose ranging effects of Oralin versus s.c. regular insulin in Type 1 diabetic patients", Fourth Annual Diabetes Technology Meeting, Philadelphia, PA 2004.
Raskin, et al., "Continuous Subcutaneous Insulin Infusion and Multiple Daily Injection Therapy are Equally Effective in Type 2 Diabetes", Diabetes Care, vol. 26, No. 9, pp. 2598-2603, Sep. 2003.
Cheatham, et al., "Desirable dynamics & performance of inhaled Insulin Compared to Subcutaneous Insulin Given at Mealtime in Type 2 Diabetes: A Report from the Technosphere/Insulin Study Group", pp. 234-235, 2004.
Cernea, et al., "Dose-Response Relationship of Oral Insulin Spray in Healthy Subjects", Diabetes Care, Vo. 28, No. 6, pp. 1353-1357, Jun. 2005.
Warren, et al., "Postprandial versus preprandial dosing of biphasic insulin aspart in elderly type 2 diabetes patients", Diabetes Research and Clinical Practice, vol. 66, pp. 23-29, 2004.
Farr, SJ et al. "Pulmonary insulin administration using the AERx(R) system: physiological and physiochemical factors influencing insulin effectiveness in healthy fasting subjects." Diabetes Tech. Ther. 2:185-197, 2000.
Hussain A and Ahsan F "State of insulin self-association does not affects its absorption from the pulmonary route." Eur. J. Pharm. Sciences 25:289-298, 2005.

* cited by examiner

*Primary Examiner* — Christina Bradley
(74) *Attorney, Agent, or Firm* — K&L Gates LLP; Louis C. Cullman; Michelle Glasky Bergman

(57) ABSTRACT

Methods related to the treatment of diabetes and improving the control of blood glucose levels are provided. In particular, methods are provided for effectively reducing postprandial glucose excursions while reducing the incidence of clinically significant late postprandial hypoglycemia by administered an insulin composition in a form suitable for pulmonary administration. Additionally, methods for effectively reducing post-prandial glucose excursions while reducing the incidence of clinically significant late postprandial hypoglycemia by administered an insulin composition in a form suitable for pulmonary administration along with a long-acting basal insulin.

16 Claims, 19 Drawing Sheets

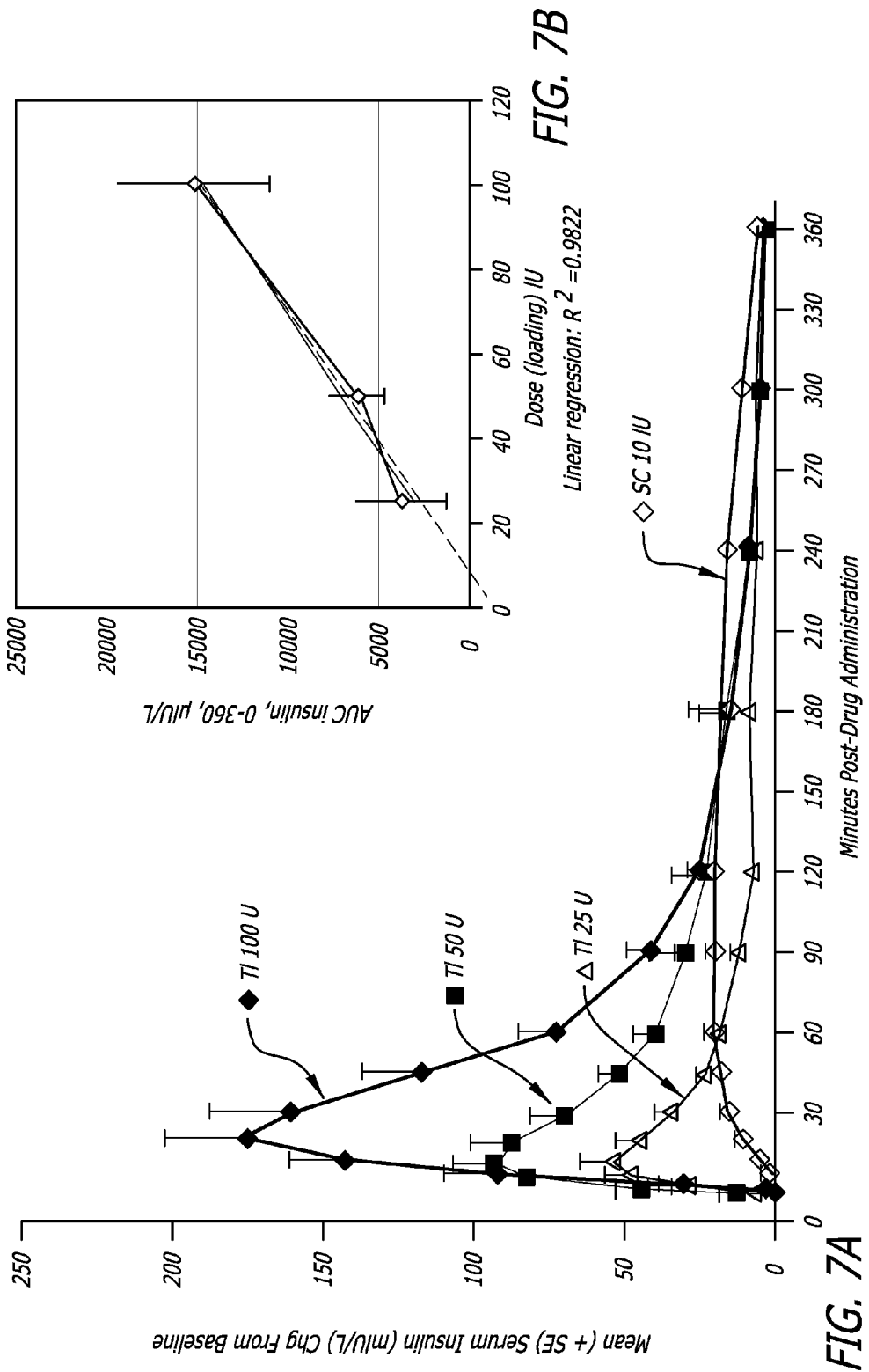

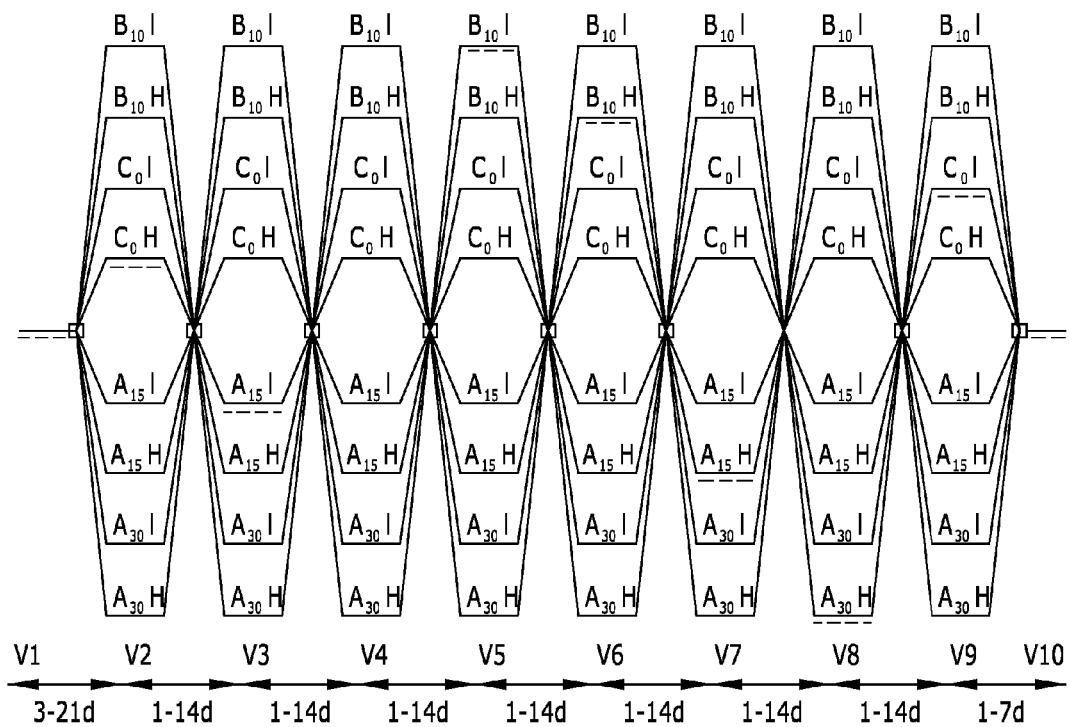

FIG. 20

- - - - - - *example for one patient*

$B_{10}$ I — *Inhalation of Technosphere/Insulin 10 min BEFORE isocaloric meal*

$B_{10}$ H — *Inhalation of Technosphere/Insulin 10 min BEFORE hypercaloric meal*

$C_0$ I — *Inhalation of Technosphere/Insulin DIRECTLY PRIOR TO isocaloric meal*

$C_0$ H — *Inhalation of Technosphere/Insulin DIRECTLY PRIOR TO hypercaloric meal*

$A_{15}$ I — *Inhalation of Technosphere/Insulin 15 min AFTER isocaloric meal*

$A_{15}$ H — *Inhalation of Technosphere/Insulin 15 min AFTER hypercaloric meal*

$A_{30}$ I — *Inhalation of Technosphere/Insulin 30 min AFTER isocaloric meal*

$A_{30}$ H — *Inhalation of Technosphere/Insulin 30 min AFTER hypercaloric meal*

SUPERIOR CONTROL OF BLOOD GLUCOSE IN DIABETES TREATMENT

CROSS REFERENCE TO RELATED APPLICATIONS

This application claims priority under 35 U.S.C. §119(e) to U.S. Provisional Patent Application No. 60/667,393 filed Mar. 31, 2005 and is a continuation-in-part of U.S. patent application Ser. No. 11/329,686, filed Jan. 10, 2006, each of which are incorporated by reference herein in their entirety.

FIELD OF THE INVENTION

The present invention relates to methods of treating diabetes and improving control of blood glucose. Specifically, the method of the present invention provides superior control of postprandial glucose levels while reducing the risk of late postprandial hypoglycemia by mimicking the insulin response kinetics of a non-diabetic individual.

BACKGROUND TO THE INVENTION

Diabetes mellitus currently afflicts at least 200 million people worldwide. Type 1 diabetes accounts for about 10% of this number, and results from autoimmune destruction of insulin-secreting β-cells in the pancreatic islets of Langerhans. Survival depends on multiple daily insulin injections. Type 2 diabetes accounts for the remaining 90% of individuals affected, and the rate of prevalence is increasing. Type 2 diabetes is often, but not always, associated with obesity, and although previously termed late-onset or adult diabetes, is now increasingly manifest in younger individuals. It is caused by a combination of insulin resistance and inadequate insulin secretion.

In a non-stressed normal individual, the basal glucose level will tend to remain the same from day to day because of an intrinsic feedback loop. Any tendency for the plasma glucose concentration to increase is counterbalanced by an increase in insulin secretion and a suppression of glucagon secretion, which regulate hepatic glucose production (gluconeogenesis and release from glycogen stores) and tissue glucose uptake to keep the plasma glucose concentration constant. If the individual gains weight or becomes insulin resistant for any other reason, blood glucose levels will increase, resulting in increased insulin secretion to compensate for the insulin resistance. Therefore the glucose and insulin levels are modulated to minimize changes in these concentrations while relatively normal production and utilization of glucose are maintained.

Five different phases of insulin secretion have been identified: (1) basal insulin secretion wherein insulin is released in the postabsorptive state; (2) the cephalic phase wherein insulin secretion is triggered by the sight, smell and taste of food, before any nutrient is absorbed by the gut, mediated by pancreatic innervation; (3) first-phase insulin secretion wherein an initial burst of insulin is released within the first 5-10 minutes after the β-cell is exposed to a rapid increase in glucose, or other secretagogues; (4) second-phase insulin secretion wherein the insulin levels rise more gradually and are related to the degree and duration of the stimulus and (5) a third-phase of insulin secretion that has only been described in vitro. During these stages, insulin is secreted, like many other hormones, in a pulsatile fashion, resulting in oscillatory concentrations in the blood. Oscillations include rapid pulses (occurring every 8-15 minutes) superimposed on slower oscillations (occurring every 80-120 minutes) that are related to fluctuations in blood glucose concentration.

Insulin secretion can be induced by other energetic substrates besides glucose (particularly amino acids) as well as by hormones and drugs. Of note is that the insulin response observed after food ingestion cannot be accounted for solely by the increase in blood glucose levels, but also depends on other factors such as the presence of free fatty acids and other secretagogues in the meal, the neurally activated cephalic phase and gastrointestinal hormones.

When an individual is given an intravenous glucose challenge, a biphasic insulin response is seen which includes a rapid increase with a peak, an interpeak nadir and a subsequent slower increasing phase. This biphasic response is only seen when glucose concentration increases rapidly, such as after a glucose bolus or glucose infusion. A slower increase in glucose administration, what is seen under physiologic conditions, induces a more gradually increasing insulin secretion without the well-defined biphasic response seen in response to bolus infusion of glucose.

Modeling of first-phase insulin responses under normal physiologic conditions has demonstrated that, after a meal, glucose concentration increases more gradually ($C_{max}$ reached in approximately 20 minutes) than seen with intravenous bolus injections of glucose ($C_{max}$ reached in approximately 3-10 minutes).

Healthy pancreatic β-cells generate an early response to a meal-like glucose exposure that rapidly elevates serum insulin both in the portal circulation and in the periphery. Conversely, defective β-cells, which have an impaired first-phase insulin response, generate a sluggish response to the meal-like glucose exposure.

Increasingly, evidence indicates that an early relatively rapid insulin response following glucose ingestion plays a critical role in the maintenance of postprandial glucose homeostasis. An early surge in insulin concentration can limit initial glucose excursions, mainly through the inhibition of endogenous glucose production. Therefore the induction of a rapid insulin response in a diabetic individual is expected to produce improved blood glucose homeostasis.

In a normal individual, a meal induces the secretion of a burst of insulin, generating a relatively rapid spike in serum insulin concentration that then decays relatively quickly (see FIG. 1). This early-phase insulin response is responsible for the shut-off of release of glucose from the liver. Homeostatic mechanisms then match insulin secretion (and serum insulin levels) to the glucose load. This is observed as a slow decay of modestly elevated serum insulin levels back to baseline and is second-phase kinetics.

Type 2 diabetics typically exhibit a delayed response to increases in blood glucose levels. While normal individuals usually begin to release insulin within 2-3 minutes following the consumption of food, type 2 diabetics may not secrete endogenous insulin until blood glucose begins to rise, and then with second-phase kinetics, that is a slow rise to an extended plateau in concentration. As a result, endogenous glucose production is not shut off and continues after consumption and the patient experiences hyperglycemia (elevated blood glucose levels).

Loss of eating-induced insulin secretion is one of the earliest disturbances of β-cell function. While genetic factors play an important role, some insulin secretory disturbances seem to be acquired and may be at least partly reversible through optimal glucose control. Optimal glucose control via insulin therapy after a meal can lead to a significant improvement in natural glucose-induced insulin release by requiring both normal tissue responsiveness to administered insulin and an abrupt increase in serum insulin concentrations. Therefore, the challenge presented in treatment of early stage type 2 diabetics, those who do not have excessive loss of β-cell function, is to restore the rapid increase in insulin following meals.

In addition to the loss of first-phase kinetics, early stage type 2 diabetics do not shut-off endogenous glucose release after a meal. As the disease progresses, the demands placed on the pancreas further degrades its ability to produce insulin and control of blood glucose levels gradually deteriorates. If unchecked, the disease can progress to the point that the deficit in insulin production approaches that typical of fully developed type 1 diabetes. However, type 1 diabetes can involve an early "honeymoon" stage, following an initial crisis, in which insulin is still produced but defects in release similar to early type 2 disease are exhibited.

Most early stage type 2 diabetics are currently treated with oral agents, but with limited success. Subcutaneous injections are also rarely ideal in providing insulin to type 2 diabetics and may actually worsen insulin action because of delayed, variable and shallow onset of action. It has been shown, however, that if insulin is administered intravenously with a meal, early stage type 2 diabetics experience the shutdown of hepatic glucose release and exhibit increased physiologic glucose control. In addition their free fatty acids levels fall at a faster rate that without insulin therapy. While possibly effective in treating type 2 diabetes, intravenous administration of insulin, is not a reasonable solution, as it is not safe or feasible for patients to intravenously administer insulin at every meal.

Significant pathology (and morbidity) in diabetics is associated with inadequate control of blood glucose. Excursions of blood glucose concentration both above and below the desired, normal range are problematic. In treatments that fail to mimic physiologic insulin release, the rise in insulin concentration does not produce sufficiently high glucose elimination rates to completely respond to the glucose load resulting from a meal. This can be further exacerbated by failure to shut off glucose release from the liver. Additionally, with many forms of insulin therapy, serum insulin levels and glucose elimination rates also remain elevated after the prandial glucose load has abated, threatening hypoglycemia. Attempts to better control peak glucose loads by increasing insulin dose further increase this danger. Indeed, postprandial hypoglycemia is a common result of insulin therapy often causing, or even necessitating, patients to eat snacks between meals, depending on the severity of hypoglycemia. This contributes to the weight gain often associated with insulin therapy. These risks and their frequency and severity of occurrence are well understood in the art.

Current insulin therapy modalities can supplement or replace endogenously-produced insulin to provide basal and second-phase-like profiles but do not mimic first-phase kinetics (see FIG. 2). Additionally, conventional insulin therapy often involves only one or two daily injections of insulin. However, more intensive therapy such as three or more administrations a day, providing better control of blood glucose levels, are clearly beneficial (see for example Nathan, D. M., et al., *N Engl J Med* 353:2643-53, 2005), but many patients are reluctant to accept the additional injections.

Until recently, subcutaneous (SC) injection has been the only route of delivering insulin to patients with both type 1 and type 2 diabetes. However, SC insulin administration does not lead to optimal pharmacodynamics for the administered insulin. Absorption into the blood (even with rapid acting insulin analogues) does not mimic the prandial physiologic insulin secretion pattern of a rapid spike in serum insulin concentration. Since the discovery of insulin, alternative routes of administration have been investigated for their feasibility in improving the pharmacodynamics of the administered insulin and improving compliance by reducing the discomfort associated with SC injections.

The alternative routes of insulin administration which have been evaluated in detail include the dermal, oral, buccal, nasal and pulmonary routes. Dermal insulin application does not result in reproducible and sufficient transfer of insulin across the highly efficient skin barrier. Effective oral insulin administration has not yet been achieved, primarily due to digestion of the protein and lack of a specific peptide carrier system in the gut. Nasal insulin application leads to a more rapid absorption of insulin across the nasal mucosa, however not with first-phase kinetics. The relative bioavailability of nasal administered insulin is low and there is a high rate of side effects and treatment failures. Buccally absorbed insulin also fails to mimic a first-phase release (Raz, I. et al., Fourth Annual Diabetes Meeting, Philadelphia, Pa., 2004).

Recently, pulmonary application of insulin has become a viable insulin delivery system. Some pulmonary insulin formulations in development provide faster appearance of insulin in the blood than typical subcutaneously delivered products (see FIG. 3), but apparently do not adequately reproduce all aspects of first-phase kinetics.

Therefore, a need exists for an insulin formulation which can mimic first-phase kinetics to provide physiologic postprandial insulin pharmacokinetics and pharmacodynamics for improved control of blood glucose levels.

SUMMARY OF THE INVENTION

The present invention provides methods of treating diabetes and yielding superior control of blood glucose levels in patient with diabetes. The method enables reassertion of homeostatic control of postprandial glucose levels while reducing the risk of hypoglycemia by administering an inhaled insulin composition at or shortly after the beginning of a meal which mimics the insulin release kinetics of a non-diabetic individual.

In one embodiment according to the present invention, a method of reducing postprandial glucose excursions in a patient with an insulin-related disorder is provided comprising administering an insulin composition in a form suitable for pulmonary administration wherein the incidence of clinically relevant late postprandial hypoglycemia is reduced.

In another embodiment according to the present invention, the insulin composition is administered in proximity to beginning a meal. In one embodiment the insulin composition is administered from approximately 10 minutes prior to beginning a meal to approximately 30 minutes after beginning a meal.

In yet another embodiment, the insulin composition comprises a complex between a diketopiperazine and human insulin and the diketopiperazine is fumaryl diketopiperazine. In an embodiment according to the present invention, the composition is administered by inhalation as a dry powder.

In yet another embodiment of the present invention, the method of reducing postprandial glucose excursions in a patient with an insulin-related disorder is provided comprising administering an insulin composition in a form suitable for pulmonary administration wherein the incidence of clinically relevant late postprandial hypoglycemia is reduced further comprises administering a long-acting basal insulin.

In an embodiment, the insulin-related disorder is diabetes mellitus. In another embodiment, the insulin-related disorder is type 2 diabetes mellitus. In yet another embodiment, the insulin-related disorder is type 1 diabetes mellitus.

In another embodiment, a method is provided for reducing postprandial glucose excursions in a patient with an insulin-related disorder comprising administering an insulin composition in a form suitable for pulmonary administration, wherein the postprandial glucose excursions are less that the postprandial glucose excursions resulting from a dose of subcutaneously administered insulin providing substantially similar insulin exposure and wherein the mean glucose excursion is at least about 25% less than for subcutaneous administration.

In yet another embodiment, the postprandial glucose excursions are reduced from those produced by treatment with an appropriate subcutaneous dose of insulin alone.

In another embodiment, the frequency of episodes of clinically relevant late postprandial hypoglycemia are reduced compared to treatment with an appropriate subcutaneous dose of insulin alone.

In another embodiment according to the present invention, a method of reducing postprandial glucose excursions in a patient with an insulin-related disorder is provided comprising administering an inhaled insulin composition comprising human insulin and fumaryl diketopiperazine in proximity to beginning a meal wherein the incidence of clinically relevant late postprandial hypoglycemia is reduced. In one embodiment the insulin composition is administered from approximately 10 minutes prior to beginning a meal to approximately 30 minutes after beginning a meal. In another embodiment, the insulin-related disorder is diabetes mellitus. In yet another embodiment, the method further comprises administering a long-acting basal insulin.

In one embodiment according to the present invention, a method of reducing postprandial glucose excursions in a patient with an insulin-related disorder being treated with basal insulin is provided comprising administering an inhaled insulin composition comprising human insulin and fumaryl diketopiperazine in proximity to beginning a meal, wherein the incidence of clinically relevant late postprandial hypoglycemia is reduced.

In another embodiment of the present invention, a method is provided for reducing postprandial glucose excursions in a patient with an insulin-related disorder comprising administering an insulin composition in a form suitable for pulmonary administration wherein the patient's total insulin exposure (INS-AUC$_{0-y}$, $3 \leq y \leq 6$ hours) does not substantially exceed that produced by an appropriate subcutaneous dose of insulin, and wherein postprandial glucose excursion is reduced. In yet another embodiment of the method, the risk of late postprandial hypoglycemia is not increased.

BRIEF DESCRIPTION OF THE DRAWINGS

FIGS. 7A-B depict the mean serum insulin concentration (FIG. 7A) and insulin absorption, as AUC (FIG. 7B), in individuals with type 2 diabetes mellitus at different dose levels of TI and SC insulin according to the teachings of the present invention.

and forced vital capacity (FVC, FIG. 19B) over time in a three month placebo-controlled clinical study with TI according to the teachings of the present invention.

FIG. 20 depicts the study schema for the clinical trial disclosed in Example 6.

Figure 21A:
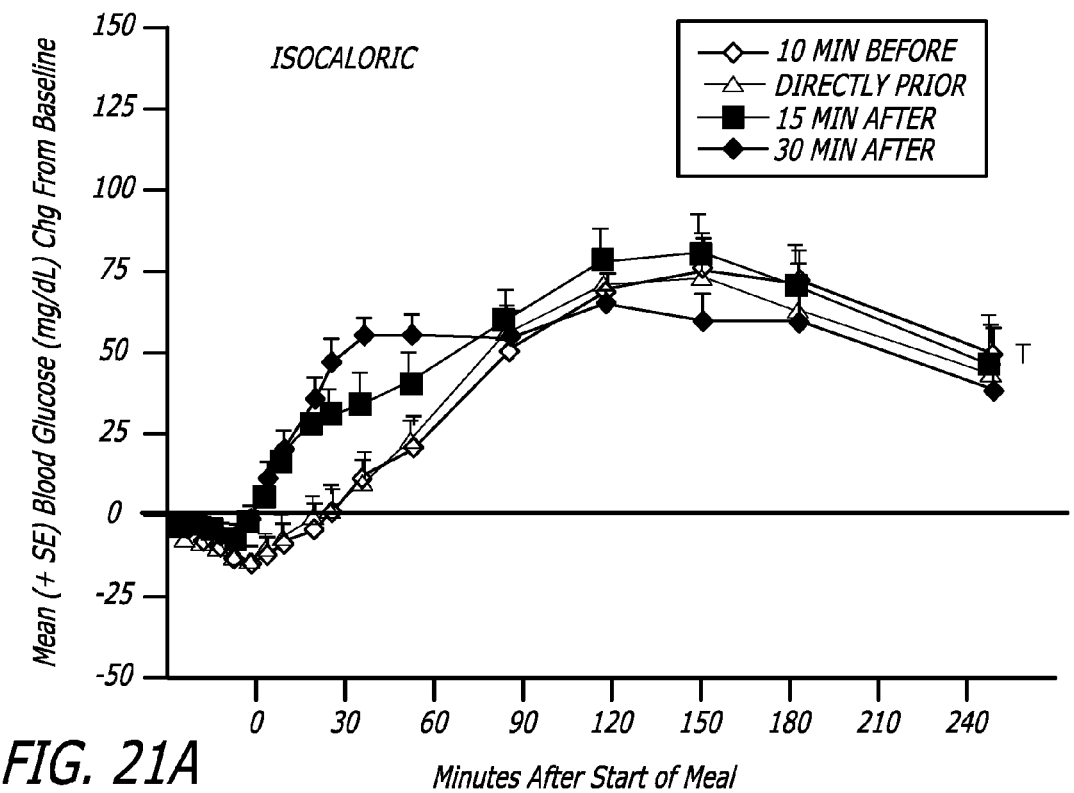
Figure 21B:
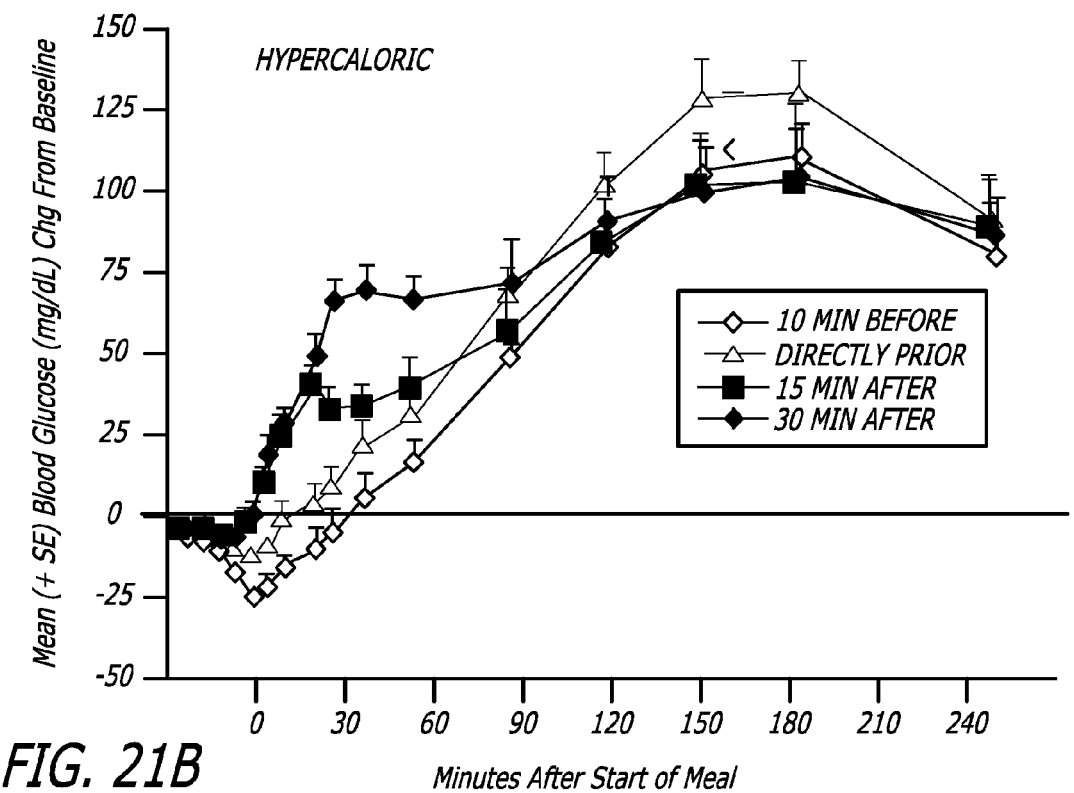

FIGS. 21A-B depict the baseline-corrected blood glucose concentration versus time by treatment group after administration of TI and a isocaloric meal (FIG. 21A) or a hypercaloric meal (FIG. 21B) according to the teachings of the present invention.

Figure 22A:
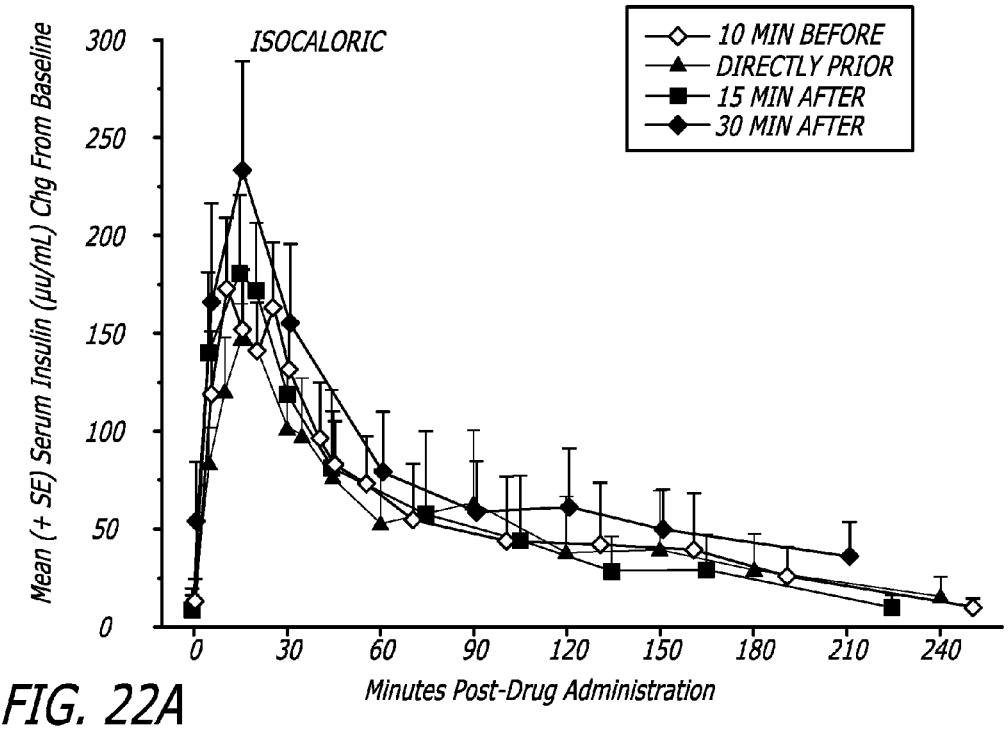
Figure 22B:
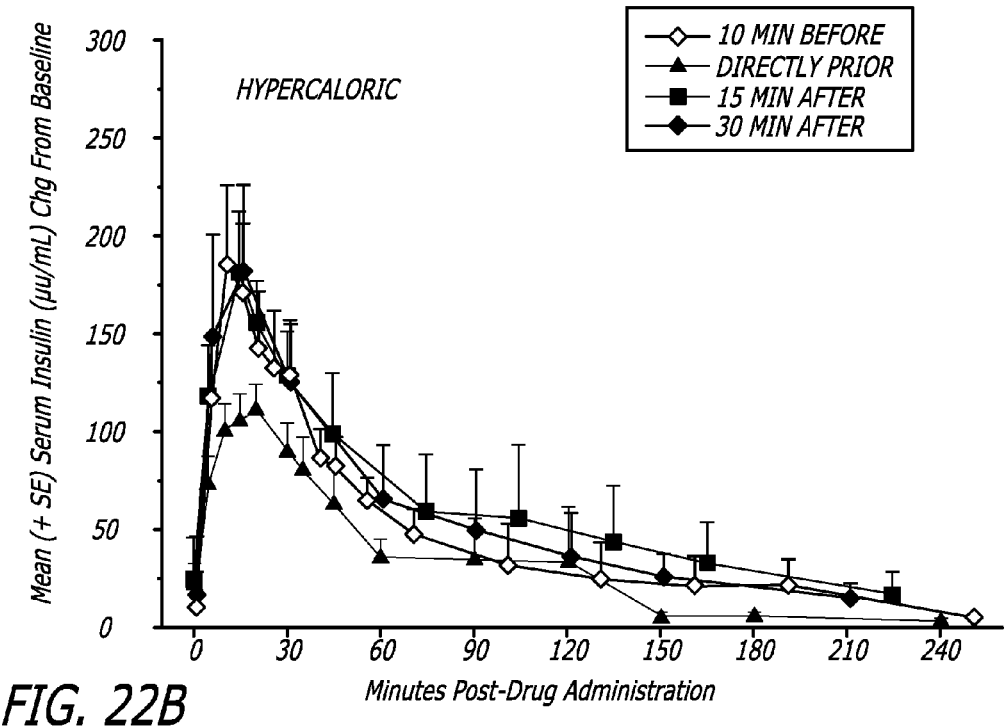

FIGS. 22A-B depict the baseline-corrected serum insulin concentration versus time by treatment group after administration of TI and a isocaloric meal (FIG. 22A) or a hypercaloric meal (FIG. 22B) according to the teachings of the present invention.

Figure 23A:
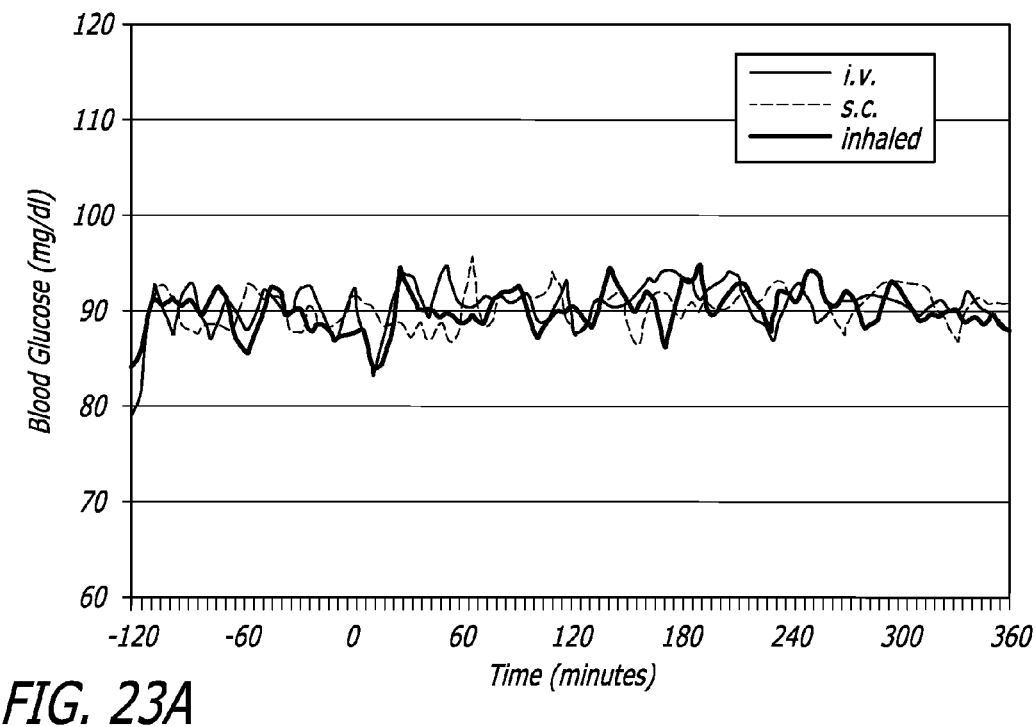
Figure 23B:
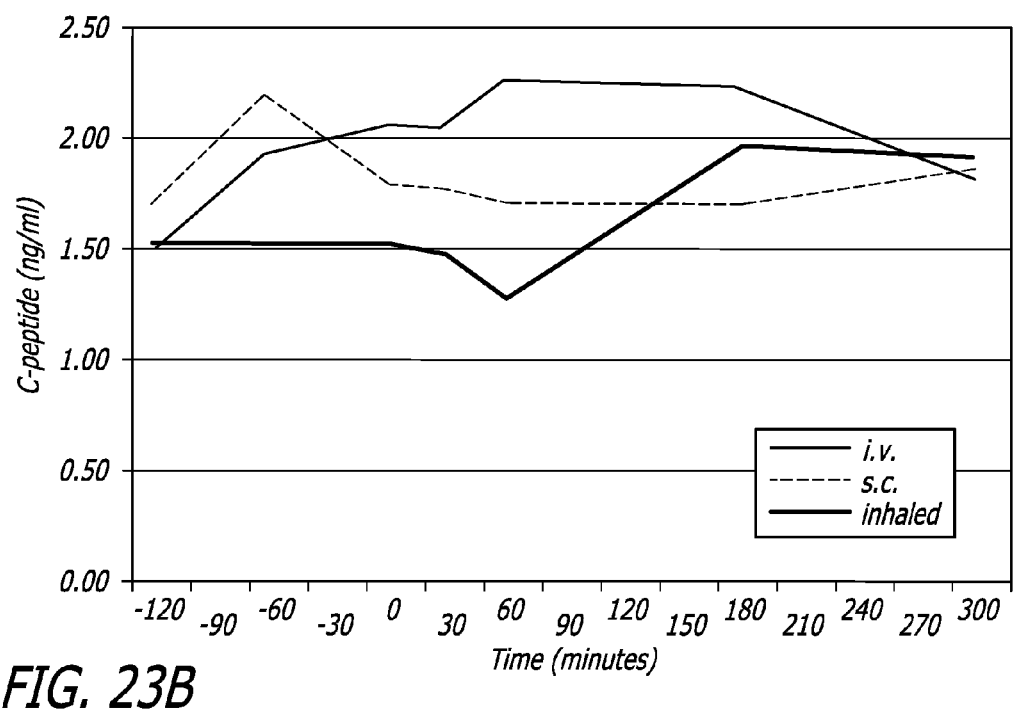

FIGS. 23A-B depict the mean blood glucose levels (FIG. 23A) or C-peptide levels (FIG. 23B) over time after administration of IV, SC or TI (inhaled) insulin according to the teachings of the present invention.

Figure 24A:
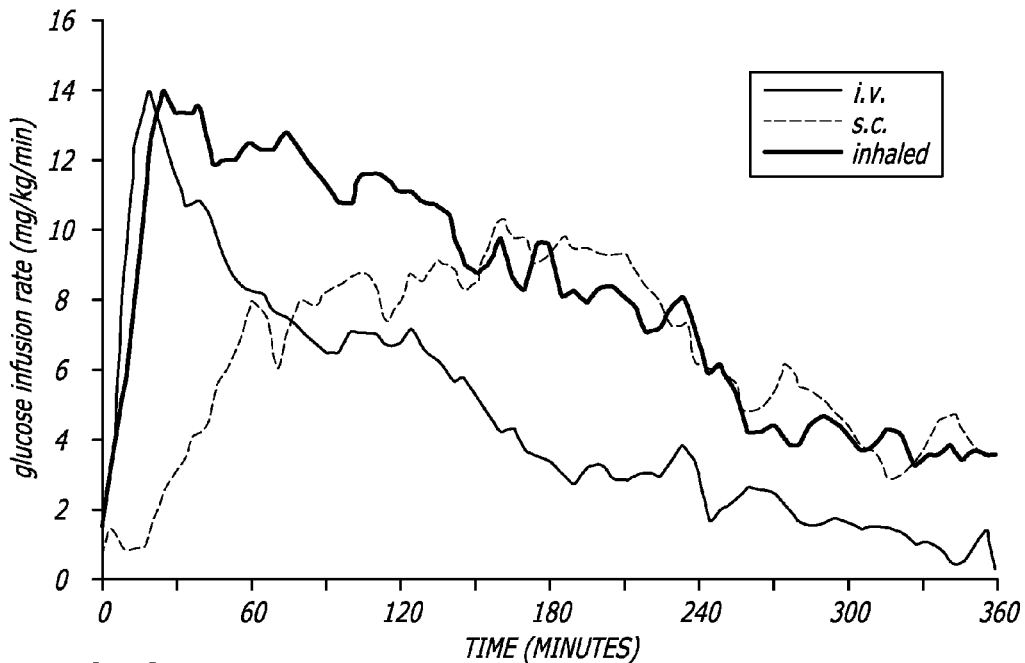
Figure 24B:
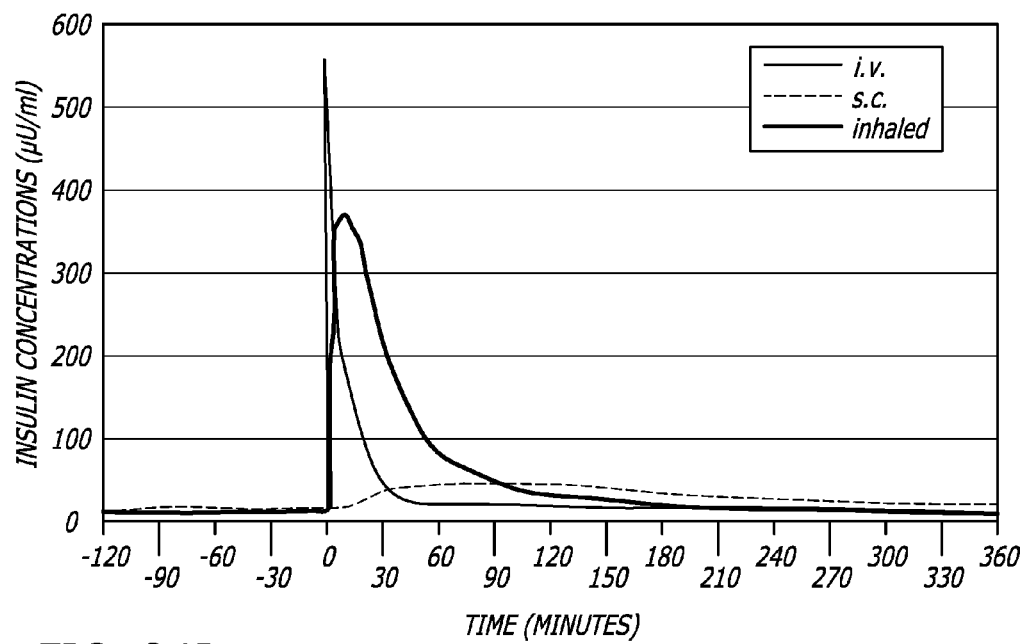

FIGS. 24A-B depict glucose infusion rate (FIG. 24A) or mean insulin concentration (FIG. 24B) over time after administration of IV, SC or TI (inhaled) insulin according to the teachings of the present invention.

DEFINITION OF TERMS

Prior to setting forth the invention, it may be helpful to provide an understanding of certain terms that will be used hereinafter:

Dry powder: As used herein "dry powder" refers to a fine particulate composition that is not suspended or dissolved in a propellant, carrier, or other liquid. It is not meant to imply a complete absence of all water molecules.

Early phase: As used herein "early phase" refers to the rise in blood insulin concentration induced in response to a meal. This early rise in insulin in response to a meal is sometimes referred to as first-phase.

Excursion: As used herein, "excursion" refers to blood glucose concentrations that fall either above or below a premeal baseline or other starting point. Excursions are generally expressed as the area under the curve (AUC) of a plot of blood glucose over time. AUC can be expressed in a variety of ways. In some instances there will be both a fall below and rise above baseline creating a positive and negative area. Some calculations will subtract the negative AUC from the positive, while others will add their absolute values. The positive and negative AUCs can also be considered separately. More sophisticated statistical evaluations can also be used. In some instances it can also refer to blood glucose concentrations that rise or fall outside a normal range. A normal blood glucose concentration is usually between 70 and 110 mg/dL from a fasting individual, less than 120 mg/dL two hours after eating a meal, and less than 180 mg/dL after eating.

First-Phase: As used herein, "first-phase" refers to the spike in insulin levels as induced by a bolus intravenous injection of glucose. A first-phase insulin release generates a spike in blood insulin concentration that is a rapid peak which then decays relatively quickly.

Glucose Elimination Rate: As used herein, "glucose elimination rate" is the rate at which glucose disappears from the blood and is determine by the amount of glucose infusion required to maintain stable blood glucose, often around 120 mg/dL during the study period. This glucose elimination rate is equal to the glucose infusion rate, abbreviated as GIR.

Hyperglycemia: As used herein, "hyperglycemia" is a higher than normal fasting blood glucose concentration, usually 126 mg/dL or higher. In some studies hyperglycemic episodes were defined as blood glucose concentrations exceeding 280 mg/dL (15.6 mM).

Hypoglycemia: As used herein, "hypoglycemia" is a lower than normal blood glucose concentration, usually less than 63 mg/dL 3.5 mM). Clinically relevant hypoglycemia is defined as blood glucose concentration below 63 mg/dL or causing patient symptoms such as hypotonia, flush and weakness that are recognized symptoms of hypoglycemia and that disappear with appropriate caloric intake. Severe hypoglycemia is defined as a hypoglycemic episode that required glucagon injections, glucose infusions, or help by another party.

In proximity: As used herein, "in proximity," as used in relation to a meal, refers to a period near in time to the beginning of a meal.

Insulin Composition: As used herein, "insulin composition" refers to any form of insulin suitable for administration to a mammal and includes insulin isolated from mammals, recombinant insulin, insulin associated with other molecules and also includes insulin administered by any route including pulmonary, subcutaneous, nasal, oral, buccal and sublingual. Insulin compositions can be formulated as dry powders or aqueous solutions for inhalation; aqueous solutions for subcutaneous, sublingual, buccal, nasal or oral administration and solid dosage forms for oral and sublingual administration.

Insulin-Related Disorder: As used herein, "insulin-related disorders" refers to disorders involving production, regulation, metabolism, and action of insulin in a mammal. Insulin related disorders include, but are not limited to, type 1 diabetes mellitus, type 2 diabetes mellitus, hypoglycemia, hyperglycemia, insulin resistance, loss of pancreatic beta cell function and loss of pancreatic beta cells.

Microparticles: As used herein, the term "microparticles" includes microcapsules having an outer shell composed of either a diketopiperazine alone or a combination of a diketopiperazine and one or more drugs. It also includes microspheres containing drug dispersed throughout the sphere; particles of irregular shape; and particles in which the drug is coated in the surface(s) of the particle or fills voids therein.

Periprandial: As used herein, "periprandial" refers to a period of time starting shortly before and ending shortly after the ingestion of a meal or snack.

Postprandial: As used herein, "postprandial" refers to a period of time after ingestion of a meal or snack. As used herein, late postprandial refers to a period of time 3, 4, or more hours after ingestion of a meal or snack.

Potentiation: Generally, potentiation refers to a condition or action that increases the effectiveness or activity of some agent over the level that the agent would otherwise attain. Similarly it may refer directly to the increased effect or activity. As used herein, "potentiation" particularly refers to the ability of elevated blood insulin concentrations to boost effectiveness of subsequent insulin levels to, for example, raise the glucose elimination rate.

Prandial: As used herein, "prandial" refers to a meal or a snack.

Second-Phase: As used herein, "second-phase" refers to the slow decay of modestly elevated blood insulin levels back to baseline after the first-phase has passed. Second-phase can also refer to the non-spiking release of insulin in response to elevated blood glucose levels.

TECHNOSPHERE®/Insulin: As used herein, "TECHNOSPHERE®/Insulin" or "TI" refers to an insulin composition comprising regular human insulin and TECHNOSPHERE®microparticles, a drug delivery system. TECHNOSPHERE® microparticles comprise a diketopiperazine, specifically 3,6-di(fumaryl-4-aminobutyl)-2,5-diketopiperazine (fumaryl diketopiperazine, FDKP). Specifically, TECHNOSPHERE®/Insulin comprises a FDKP/human insulin composition.

As used herein, "diketopiperazine" or "DKP" includes diketopiperazines and salts, derivatives, analogs and modifications thereof falling within the scope of the general Formula 1, wherein the ring atoms $E_1$ and $E_2$ at positions 1 and 4 are either O or N and at least one of the side-chains $R_1$ and $R_2$ located at positions 3 and 6 respectively contains a carboxylic acid (carboxylate) group. Compounds according to Formula 1 include, without limitation, diketopiperazines, diketomorpholines and diketodioxanes and their substitution analogs.

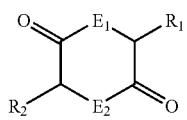

Formula 1

Diketopiperazines, in addition to making aerodynamically suitable microparticles, also facilitate transport across cell layers, further speeding absorption into the circulation. Diketopiperazines can be formed into particles that incorporate a drug or particles onto which a drug can be adsorbed. The combination of a drug and a diketopiperazine can impart improved drug stability. These particles can be administered by various routes of administration. As dry powders these particles can be delivered by inhalation to specific areas of the respiratory system, depending on particle size. Additionally, the particles can be made small enough for incorporation into an intravenous suspension dosage form. Oral delivery is also possible with the particles incorporated into a suspension, tablets or capsules. Diketopiperazines may also facilitate absorption of an associated drug.

In another embodiment of the present invention, the DKP is a derivative of 3,6-di(4-aminobutyl)-2,5-diketopiperazine, which can be formed by (thermal) condensation of the amino acid lysine. Exemplary derivatives include 3,6-di(succinyl-4-aminobutyl)-, 3,6-di(maleyl-4-aminobutyl)-, 3,6-di(glutaryl-4-aminobutyl)-, 3,6-di(malonyl-4-aminobutyl)-, 3,6-di(oxalyl-4-aminobutyl)-, and 3,6-di(fumaryl-4-aminobutyl)-2,5-diketopiperazine. The use of DKPs for drug delivery is known in the art (see for example U.S. Pat. Nos. 5,352,461, 5,503,852, 6,071,497, and 6,331,318", each of which is incorporated herein by reference for all that it teaches regarding diketopiperazines and diketopiperazine-mediated drug delivery). The use of DKP salts is described in co-pending U.S. patent application Ser. No. 11/210,710 filed Aug. 23, 2005, which is hereby incorporated by reference for all it teaches regarding diketopiperazine salts. Pulmonary drug delivery using DKP microparticles is disclosed in U.S. Pat. No. 6,428,771, which is hereby incorporated by reference in its entirety.

TECHNOSPHERE®/Placebo: As used herein, "TECHNOSPHERE®/Placebo" refers to TECHNOSPHERE® particles which are not associated with insulin.

Units of measure: Subcutaneous and intravenous insulin dosages are expressed in IU which is defined by a standardized biologic measurement. Amounts of insulin formulated with fumaryl diketopiperazine are also reported in IU as are measurements of insulin in the blood. TECHNOSPHERE®/Insulin dosages are expressed in arbitrary units (U) which are numerically equivalent to the amount of insulin formulated in the dosage.

DETAILED DESCRIPTION OF THE INVENTION

A common problem with insulin therapy for the treatment of diabetes is that insulin doses sufficient to control prandial glucose loads produce elevated glucose elimination rates for extended intervals that can persist after the meal, leading to postprandial hypoglycemia. The increase in blood levels of insulin, after subcutaneous administration, is significantly slower in diabetics than the physiologic response to prandial glucose seen in normal individuals. Therefore insulin compositions and methods which result in a more rapid rise in serum insulin levels, which then decline, result in an more physiologic means to achieve maximal glucose elimination rates. This has the effect of compressing the bulk of the effect of the administered insulin to the periprandial time interval thereby reducing the risks of post-prandial hypoglycemia and resulting in a more normal physiologic insulin response to prandial glucose.

It has been generally assumed that the rate of glucose elimination at any point in time is a function of insulin concentration at that point in time. In point of fact the glucose elimination rate achieved by any particular insulin concentration is influenced by prior insulin concentration. Thus glucose elimination rate is potentiated by previous high insulin levels such that, for any particular insulin concentration, the glucose elimination rate is greater when the subject has experienced a high insulin concentration in a preceding time interval. The present inventors have now surprisingly discovered that this potentiation drives the glucose elimination rate to maximum much more quickly in response to a large and rapid peak in insulin concentration than when peak insulin concentration is approached more gradually.

When the inhaled insulin composition of the present invention, an insulin/diketopiperazine microparticle (TECHNOSPHERE®/Insulin, TI), is administered at or shortly after the beginning of a meal, blood glucose levels after the meal are more tightly controlled than if patients attempt to control their disease with subcutaneous insulin or oral medications.

Figure 1:
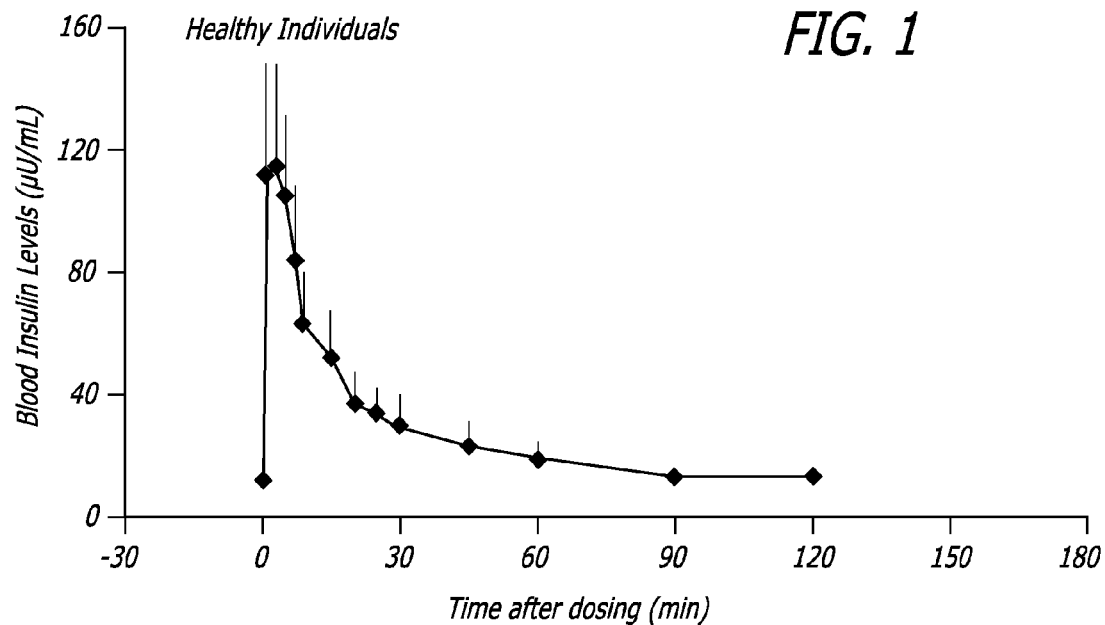
FIG. 1 depicts the measurement of first-phase insulin release kinetics following artificial stimulation by bolus glucose infusion.
Figure 2:
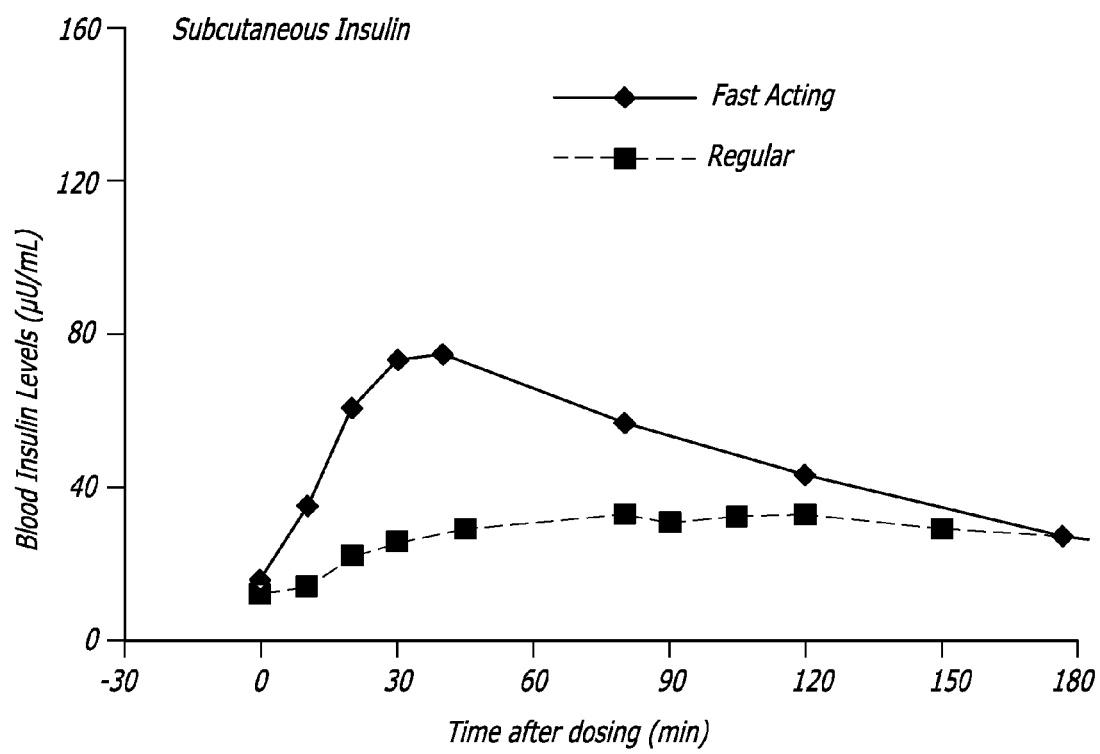
FIG. 2 depicts serum insulin concentration after administration of subcutaneous (SC) regular human insulin or SC fast acting insulin (insulin aspart: NOVOLOG™, Novo Nordisk Pharmaceuticals, Bagsvaerd, Denmark).
Figure 3:
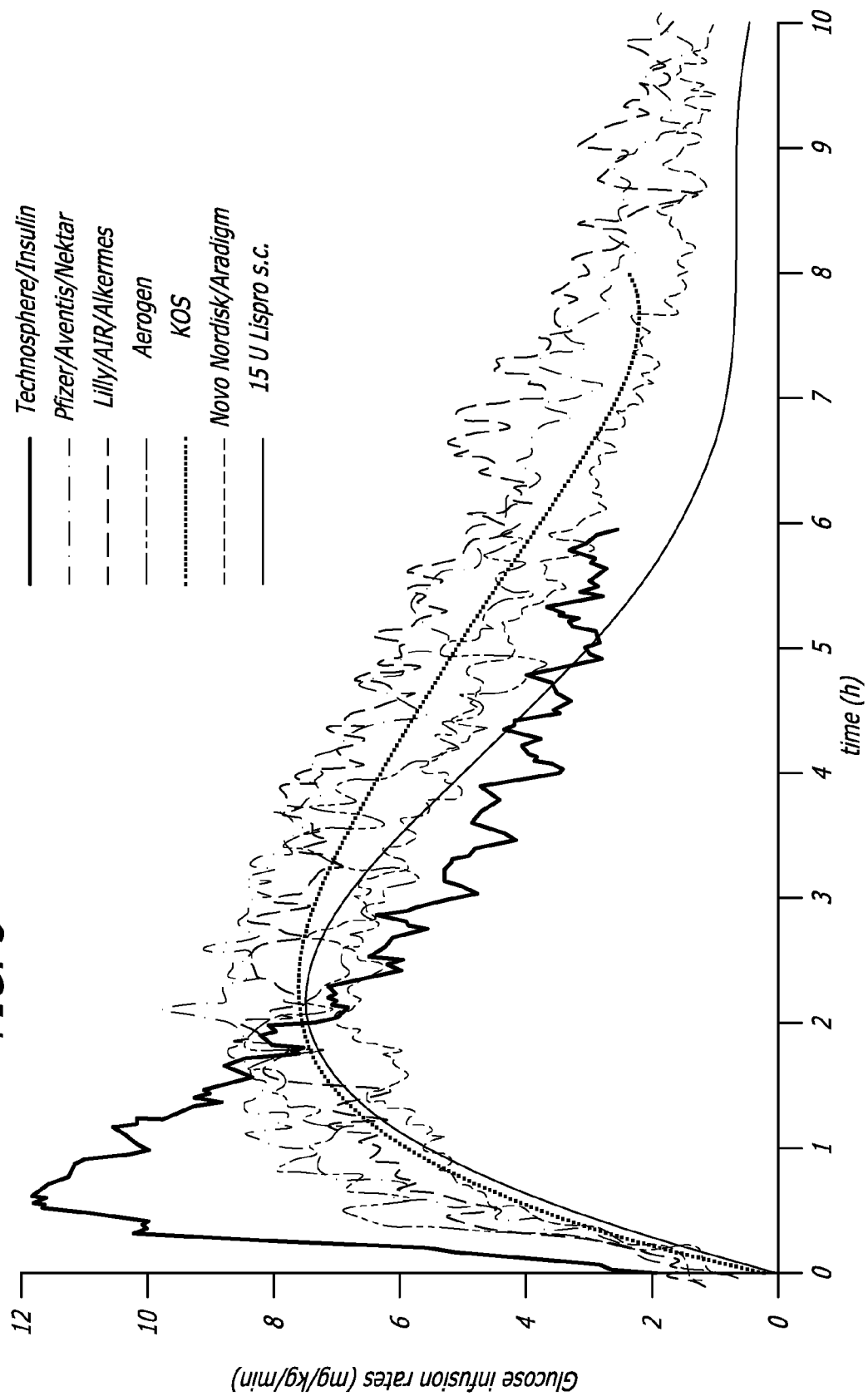
FIG. 3 depicts a composite of time-action profiles of a variety of forms of inhaled (MannKind, Pfizer/Aventis/Nektar, Alkermes, Aerogen, KOS, Novo Nordisk/Aradigm) and injected (Lispro SC) insulin from different manufacturers (from: *Br J Diab Vasc. Dis* 4:295-301, 2004).
Figure 4:
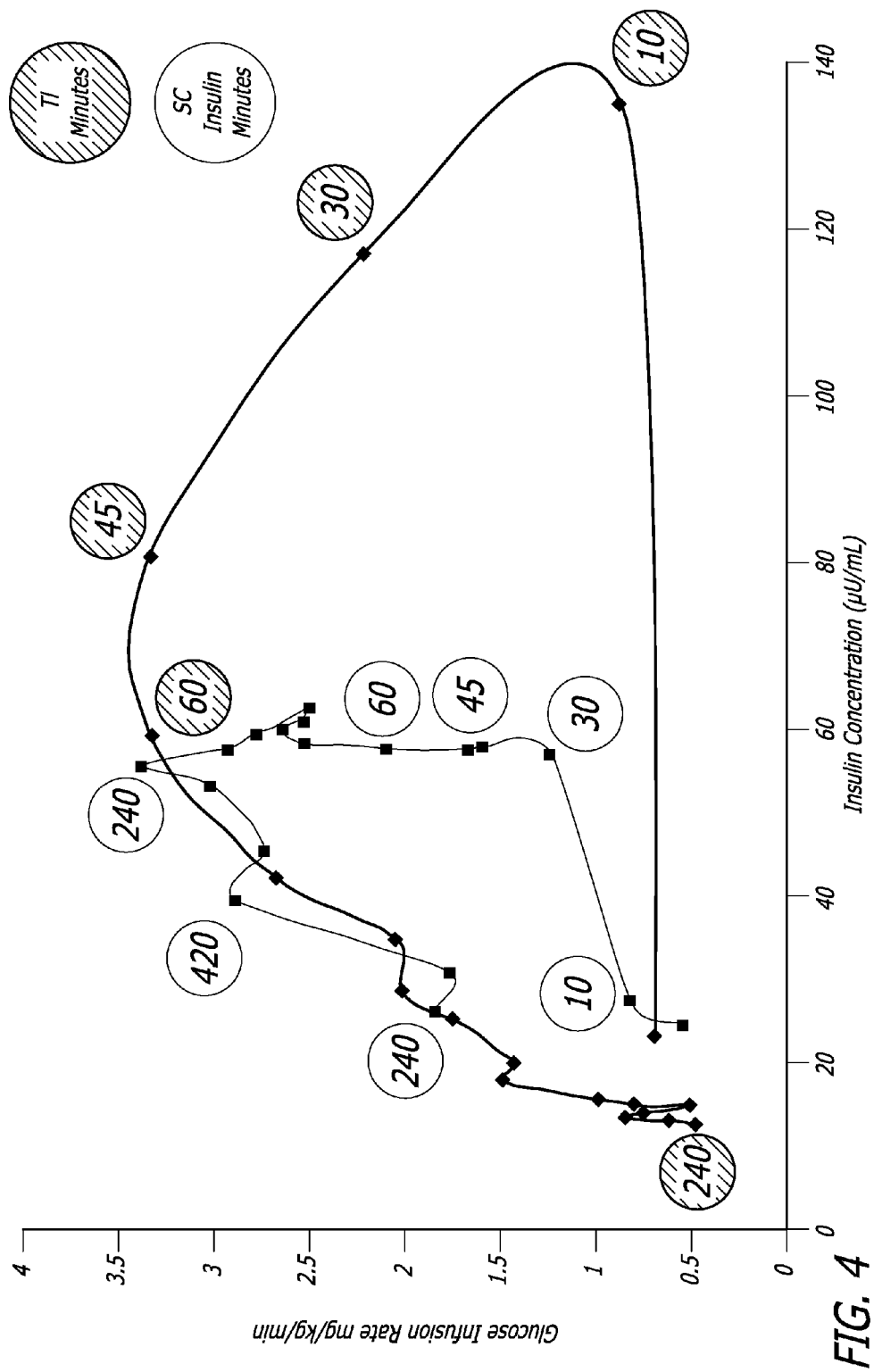
FIG. 4 depicts the relationship over time between serum insulin concentration and glucose elimination rate, as glucose infusion rate (GIR) under a glucose clamp, for a fast-acting subcutaneously administered insulin (SC) and a pulmonary dry powder insulin formulated with fumaryl diketopiperazine (TECHNOSPHERE®/Insulin, TI) according to the teachings of the present invention.
Figure 5:
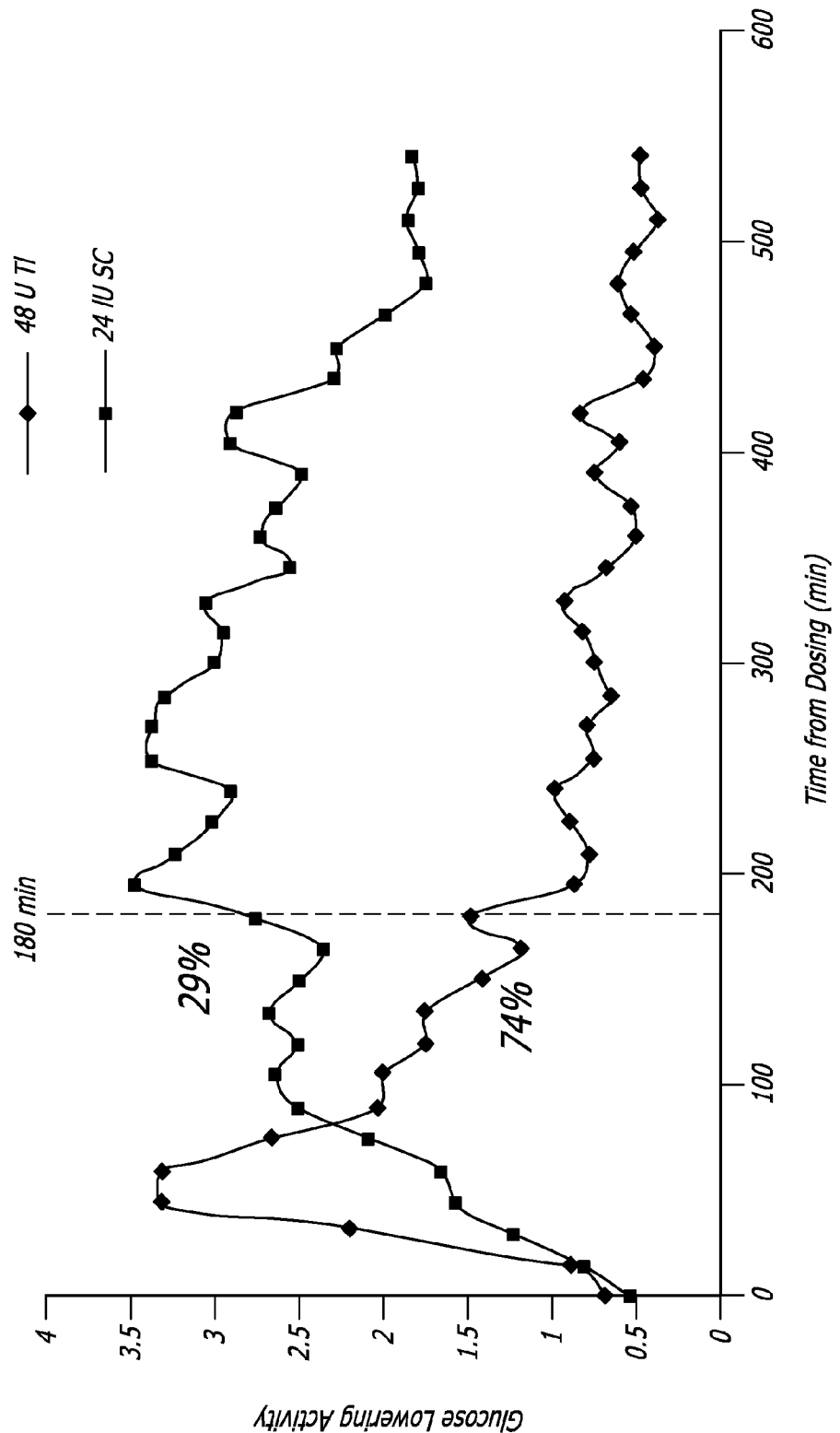
FIG. 5 depicts increased postprandial glucose elimination for TECHNOSPHERE®/Insulin (48 U TI) versus a fast-acting subcutaneously administered insulin (24 IU SC) in individuals with type 2 diabetes mellitus according to the teachings of the present invention.

With a typical fast-acting subcutaneous (SC) administered insulin, maximal insulin concentrations can be achieved in about 30 to 45 minutes and remain at this plateau for several hours (FIG. 2). The glucose elimination rate (measured as the glucose infusion rate [GIR]) however continues to rise throughout this plateau phase (FIG. 5), peaking only as insulin concentration begins to decay (FIG. 4). In contrast, with an administration that mimics a physiological first-phase insulin release, insulin concentration peaks at a much higher level and begins to fall by about 15 minutes (FIG. 1). The GIR, however, continues to rise after the peak in insulin concentration but reaches its maximum in less than an hour and then falls in concert with insulin concentration (FIG. 4). By three hours, the bulk of glucose elimination to be accomplished by this insulin has occurred, yet the subcutaneous insulin has exerted less than a third of its effect (FIG. 5).

By taking advantage of the potentiating effects of a rapid spike in insulin concentration, an insulin therapy methodology that mimics first-phase kinetics can offer several advantages. Such insulin formulations are generally administered within a few minutes of commencing a meal, unlike more slowly absorbed insulins which are usually taken at defined period before a meal. The interval is generally based on the time needed to achieve maximal insulin concentration on the tacit assumption that glucose elimination rate is a function of insulin concentration. However, since glucose elimination rate continues to increase throughout the plateau in insulin concentration, doses large enough to keep glucose levels from exceeding the normal range pose a risk that the resultant high glucose elimination rate hours after the meal will lead to hypoglycemia. Due to the potentiating effect of an insulin preparation causing a rapid peak in serum insulin concentration, it can be more readily coordinated with a meal. The quick acquisition of maximal glucose elimination rate is well suited to mealtime administration, or even up to an hour after commencing a meal. The second-phase decay in insulin concentration reduces the risk of inducing hypoglycemia hours after the meal. Further advantages are realized in diabetics who retain some ability to produce insulin in that their endogenous second-phase and basal insulin will also be potentiated, increasing the effectiveness of that limited insulin and reducing pancreatic stress. Methods of reducing pancreatic stress with the exogenously-administered insulin compositions of the present invention are disclosed in co-pending U.S. Provisional Patent Application No. 60/704,295 entitled "Methods of Preserving the Function of Insulin-Producing Cells in Diabetes," which is incorporated by reference herein for all it teaches regarding methods of reducing pancreatic stress by administering diketopiperazine/insulin compositions. The administration of exogenous insulin also suppresses insulin secretion from the pancreas. The quicker return to baseline achieved with a rapidly peaking insulin allows for earlier reassertion of pancreatic secretion and re-establishment of homeostatic control of blood glucose levels, further reducing the risk of post-treatment hypoglycemia and excursions of blood glucose levels. Similar advantages are contemplated from combined treatment with rapid-peaking and long acting exogenous insulin for diabetics who do not produce significant levels of insulin.

As used herein, mimicking physiologic mealtime or first-phase insulin release (or pharmacokinetics) does not necessarily indicate exact replication of all features of the physiologic response. It can refer to methodologies producing a spike or peak of insulin concentration in the blood that constitutes both a relatively quick rise (less than about 15 minutes from administration or first departure from baseline) and fall (descent through half maximal by 80 minutes, preferably 50 minutes, more preferably 35 minutes after peak) in concentration. This is in contrast to methods producing a more gradual rise (from over 20 minutes to several hours) to the maximal insulin concentration achieved and a prolonged plateau at near maximal concentrations. It can also refer to methodologies in which the spike in insulin concentration can be reliably coordinated with the start of a meal. It can also refer to methodologies achieving maximal glucose elimination rate within about 30-90 minutes, preferably around 45-60 minutes, after administration. A methodology that mimics first-phase release is generally also one that can be practiced by diabetics upon themselves without special medical training, such as training in intravenous injection. Special medical training would not include training to use medical devices, such as dry powder inhalers, that are routinely used by persons who are not medical professionals. As used herein, "meal", "meals", and/or "mealtime", etc. include traditional meals and meal times; however, these also include the ingestion of any sustenance regardless of size and/or timing.

Superior blood glucose control can be appreciated as reduced exposure to (elevated) glucose concentrations ($AUC_{GLU}$), reduced levels of HbA1c (glycosylated hemoglobin), lessened potential (risk) or incidence of hypoglycemia, reduced variability of response to treatment, and the like. Glycosylated hemoglobin levels correlate with the overall blood glucose control over the past three months. Generally one compares outcomes of different procedures at similar levels of exposure to insulin ($AUC_{INS}$) for various time intervals. Glucose exposure and risk of hypoglycemia ultimately depends on how well glucose elimination rate matches glucose load over time. This in turn will generally depend on the shape of the insulin concentration curve rather than simply on the area under the curve. The rapid rise and fall of insulin concentration typical of physiologic first-phase response is well suited to matching glucose elimination rate to prandial glucose load.

The desirable first-phase kinetics can be obtained through the pulmonary administration of a dry powder insulin formulation containing insulin complexed to 3,6-di(fumaryl-4-aminobutyl)-2,5-diketopiperazine (hereinafter fumaryl diketopiperazine or FDKP). The use of diketopiperazines for drug delivery is known in the art (see for example U.S. Pat. No. 5,352,461 entitled "Self Assembling Diketopiperazine Drug Delivery System; U.S. Pat. No. 5,503,852 entitled Method for Making Self-Assembling Diketopiperazine Drug Delivery System; U.S. Pat. No. 6,071,497 entitled Microparticles for Lung Delivery Comprising Diketopiperazine; and U.S. Pat. No. 6,331,318 entitled Carbon-Substituted Diketopiperazine Delivery System, each of which is incorporated herein by reference for all that they teach regarding diketopiperazines and diketopiperazine-mediated drug delivery). Pulmonary drug delivery using diketopiperazine and other microparticles is disclosed in U.S. Pat. No. 6,428,771 entitled "Method for Drug Delivery to the Pulmonary System," which is hereby incorporated by reference for all that it teaches regarding delivery of diketopiperazine-based compositions to the pulmonary system. Complexes of insulin and FDKP, their formation, properties, and use are disclosed in U.S. Pat. Nos. 6,444,226 and 6,652,885 both entitled "Purification and Stabilization of Peptide and Protein Pharmaceutical Agents," each of which is incorporated herein by reference for all that they teach regarding formation and administration of FDKP-complexed agents. Additional methods of manufacture of complexes of diketopiperazines and insulin are disclosed in co-pending U.S. Provisional Patent Application No. 60/717,524 entitled "Method of Drug Formulation Based on Increasing the Affinity of Active Agents for Crystalline Microparticle Surfaces," which is incorporated herein by reference for all it teaches regarding manufacture of complexes of diketopiperazines and insulin. Particularly advantageous devices for delivery of the powder are disclosed in U.S. patent application Ser. No. 10/655,153 entitled "Unit Dose Cartridge and Dry Powder Inhaler" and in U.S. Pat. No. 6,923,175 entitled "Inhalation Apparatus", each of which is incorporated herein by reference for all that they teach regarding pulmonary delivery of insulin compositions.

Figure 9A:
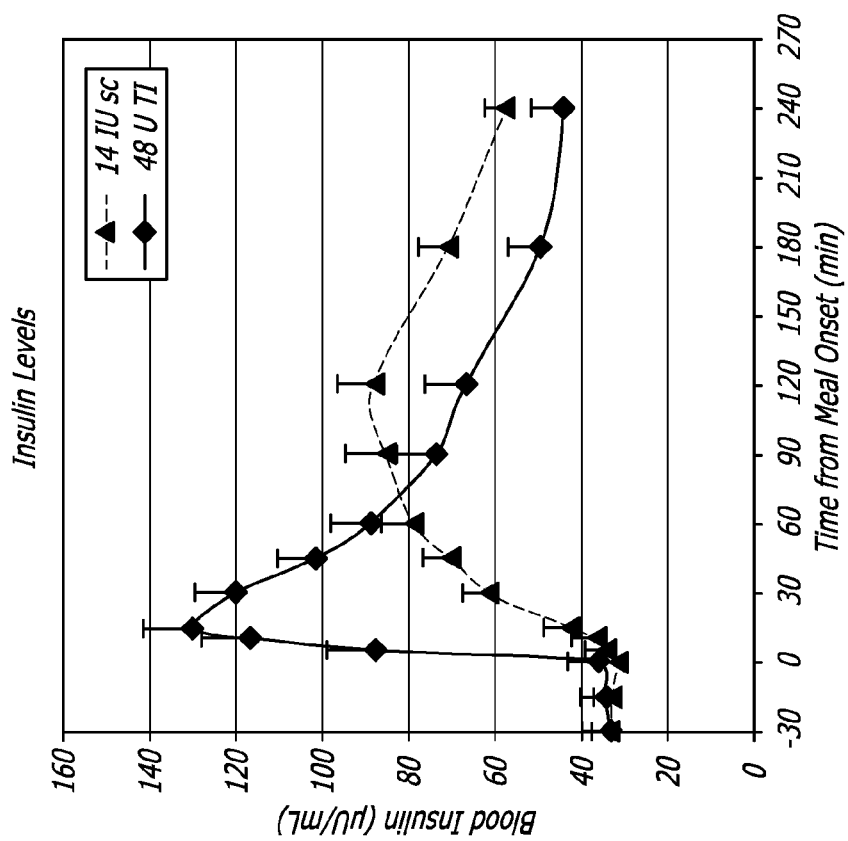
Figure 10:
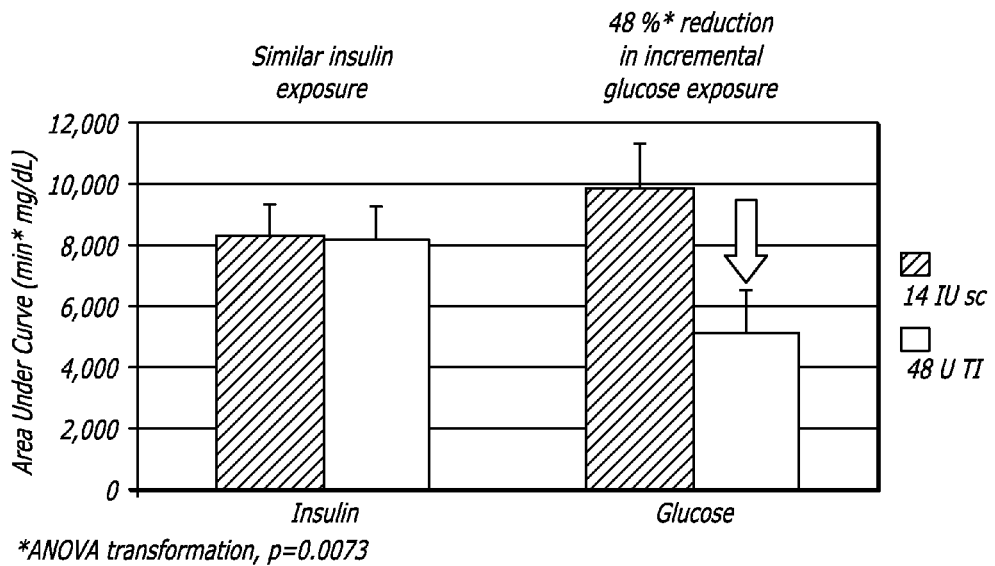
FIG. 10 depicts the improved postprandial glucose exposure with similar insulin exposure in individuals with type 2 diabetes mellitus after administration of 14 IU SC insulin or 48 U TI according to the teachings of the present invention.

Administration of TECHNOSPHERE®/Insulin, by inhalation, leads to serum insulin levels that rise more rapidly than subcutaneously administered insulin (FIG. 9A), more closely approximating the insulin response to meal-associated glucose in normal individuals. Additionally, post-meal excursions of glucose are limited after TI administration in the post-meal period to a greater extent than with SC administered insulin (FIG. 10). In controlled clinical trials, the total exposure of the patient to insulin is the same whether the patient has been administered TI or SC, however the post-meal excursions from normal blood glucose levels are significantly less (about half) with TI than with SC insulin (FIG. 10). Therefore the delivery of insulin in a manner that approximates the insulin response of healthy individuals allows patients with diabetes to achieve greater control over their blood glucose levels during the post-meal period.

Figure 17:
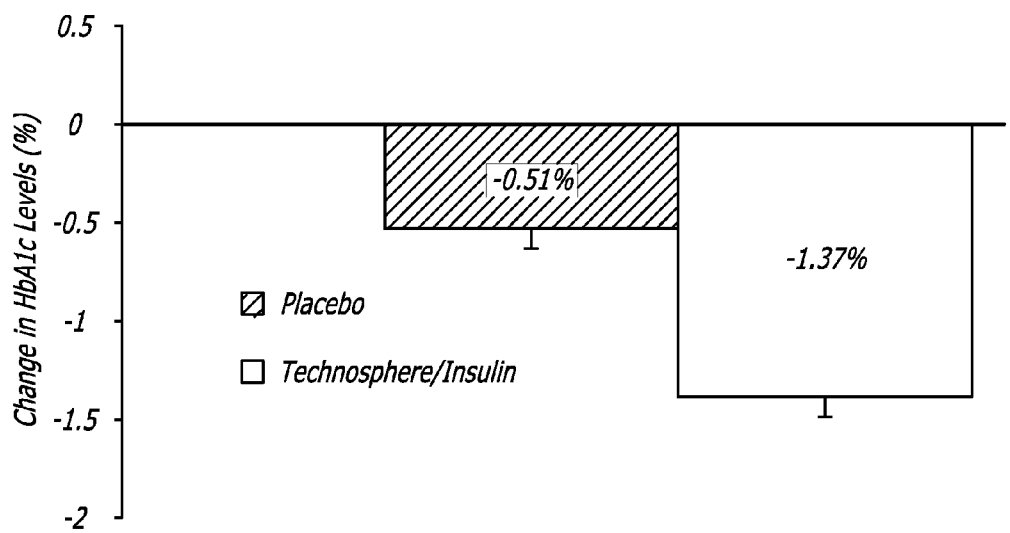
FIG. 17 depicts the change in mean glycosylated hemoglobin (HbA1c) levels after 12 weeks of administration of TI or placebo in individuals with type 2 diabetes mellitus according to the teachings of the present invention.

In patients with moderately severe elevations of HbA1c (a marker of control of blood glucose levels over a three month time period), treatment with TI resulted in a reduction of HbA1c levels compared to control-treated individuals (FIG. 17) demonstrating superior control of blood glucose levels over time with TI treatment.

Furthermore, addition of TI to regular basal insulin administration produces a statistically significant, dose-dependent reduction in HbA1c levels and a dose dependent effect on post-meal glucose excursions.

The ability of TI to substantially mimic normal insulin responses to glucose and substantially reduced post-meal glucose excursions may have additional benefits to the general health of diabetics. Excessive post-meal glucose excursions are linked to atherosclerosis and diabetic vascular disease, a complication of diabetes that affects the yeye, kinesy and peripheral autonomic nervous systems. Therefore administration of TI according to the teachings of the present invention provides superior control of blood glucose levels leading to better management of diabetic symptoms and better overall health of the diabetic patient.

Complexation of large polymers, such as proteins and peptides, in diketopiperazines can be used to remove impurities or contaminants such as metal ions or other small molecules. The diketopiperazines also serve both to stabilize and enhance delivery of the complexed materials. Formulations also have been developed facilitate transport of active agents across biological membranes. These formulations include microparticles formed of (i) the active agent, which may be charged or neutral, and (ii) a transport facilitator that masks the charge of the agent and/or that forms hydrogen bonds with the membrane. The formulations can provide rapid increases in the concentration of active agent in the blood following administration of the formulations.

TECHNOSPHERE® refers to a diketopiperazine-based drug delivery system which can complex and stabilize peptides in small particles. Diketopiperazines, particularly fumaryl diketopiperazine (FDKP), self-assemble into microparticles with a mean diameter of about 2 microns. In the process it can entrap or complex with peptides, such as insulin, present in the solution during or after self-assembly. Once dried, these microparticles become a suitable composition for pulmonary delivery to the systemic circulation. When administered by the pulmonary route, TECHNOSPHERE® particles dissolve in the pH neutral environment of the deep lung and facilitate the rapid and efficient absorption of the peptide into systemic circulation. The FDKP molecules are excreted un-metabolized in the urine within hours of administration.

Additionally, salts of diketopiperazines can be used in the compositions of the present invention as disclosed in co-pending U.S. patent application Ser. No. 11/210,710 entitled "Diketopiperazine Salts for Drug Delivery and Related Methods" which is incorporated by reference herein for all it teaches regarding diketopiperazine salts and their use to in pulmonary delivery of insulin.

Insulin, a polypeptide with a nominal molecular weight of 6,000 daltons, traditionally has been produced by processing pig and cow pancreas to isolate the natural product. More recently, however, recombinant technology has been used to produce human insulin in vitro. Natural and recombinant human insulin in aqueous solution is in a hexameric conformation, that is, six molecules of recombinant insulin are noncovalently associated in a hexameric complex when dissolved in water in the presence of zinc ions. Hexameric insulin is not rapidly absorbed. In order for recombinant human insulin to be absorbed into a patient circulation, the hexameric form must first disassociate into dimeric and/or monomeric forms before the material can move into the bloodstream.

For example, it was discovered that insulin can be delivered to the lung in fumaryl diketopiperazine formulation, reaching peak blood concentrations within 3-10 minutes. In contrast, hexameric insulin administered by the pulmonary route without fumaryl diketopiperazine typically takes between 25-60 minutes to reach peak blood concentrations, while hexameric insulin takes 30-90 minutes to reach peak blood level when administered by subcutaneous injection. This feat has been successfully replicated several times and in several species, including humans.

Removing zinc from insulin typically produces unstable insulin with an undesirably short shelf life. Purification to remove zinc, stabilization and enhanced delivery of insulin has been demonstrated using diketopiperazine microparticles. Formulations of insulin complexed with fumaryl diketopiperazine were found to be stable and have an acceptable shelf life. Measurement of the zinc levels demonstrated that when a washing step was included the zinc had been largely removed during the complexation process, yielding monomeric insulin in a stable delivery formulation.

The insulin compositions of the present invention can be administered to patients in need of insulin therapy. The compositions preferably are administered in the form of microparticles, which can be in a dry powder form for pulmonary administration or suspended in an appropriate pharmaceutical carrier, such as saline.

The microparticles preferably are stored in dry or lyophilized form until immediately before administration. The microparticles then can be administered directly as a dry powder, such as by inhalation using, for example, dry powder inhalers known in the art. Alternatively, the microparticles can be suspended in a sufficient volume of pharmaceutical carrier, for example, as an aqueous solution for administration as an aerosol. The microparticles also can be administered via oral, subcutaneous, and intravenous routes.

The inhalable insulin compositions can be administered to any targeted biological membrane, preferably a mucosal membrane of a patient. In one embodiment, the patient is a human suffering from an insulin-related disorder such as diabetes mellitus. In another embodiment, the inhalable insulin composition delivers insulin in biologically active form to the patient, which provides a spike of serum insulin concentration which simulates the normal response to eating.

In another embodiment, the inhalable insulin composition is administered to a patient in combination with long-acting basal insulin. The dose and administration of the long-acting basal insulin is established by the patient's physician according to standard medical practice. The inhalable insulin composition is administered periprandially according the teachings of the present invention, independently of the administration parameters of the basal insulin. Therefore for the purposes of this disclosure "in combination" refers to a patient administered both the inhalable insulin composition of the present invention and a long-acting basal insulin however, the two forms of insulin are administered independently.

In one embodiment of the present invention, a pharmaceutical composition is provided comprising insulin in a form suitable for pulmonary administration which, when administered in proximity in time to the beginning of a meal, induces a lower coefficient of variation at the 95% confidence interval of insulin exposure, INS-AUC$_{0-x}$, x≦3, than subcutaneously administered insulin, wherein total insulin exposure [INS-AUC$_{0-y}$, 3≦y≦6] is substantially similar.

In another embodiment of the present invention, a pharmaceutical composition is provided comprising insulin in a form suitable for pulmonary administration which, when administered in proximity in time to the beginning of a meal, induces a lower coefficient of variation at the 95% confidence interval in glucose elimination than subcutaneously administered insulin, wherein glucose elimination is measured as glucose infusion rate (GIR-)AUC$_{0-x}$, x≦3 hours, wherein total insulin exposure [INS-AUC$_{0-y}$, 3≦y≦6] is substantially similar.

In yet another embodiment of the present invention, a pharmaceutical composition is provided comprising insulin in a form suitable for pulmonary administration which, when administered in proximity in time to the beginning of a meal, produces a mean glucose excursion that is less than subcutaneous administration of a dose of insulin providing substantially similar insulin exposure wherein the mean glucose excursion is at least about 28%, particularly at least about 25%, less than for the subcutaneous administration.

In an embodiment of the present invention, a pharmaceutical composition is provided comprising insulin in a form suitable for pulmonary administration which, when administered in proximity in time to the beginning of a meal, produces a mean glucose exposure that is less than subcutaneous administration of a dose of insulin providing substantially similar insulin exposure wherein the mean glucose exposure is at least about 35% less than for the subcutaneous administration, preferably about 50% less than for the subcutaneous administration.

In another embodiment of the present invention, a pharmaceutical composition is provided comprising insulin in a form suitable for pulmonary administration which, when administered in proximity in time to the beginning of a meal, exhibits a ratio of HbA1c after treatment to HbA1c before treatment, that is less than for subcutaneous administration of a dose of insulin providing substantially similar insulin exposure.

In an embodiment of the present invention, a pharmaceutical composition is provided comprising insulin in a form suitable for pulmonary administration which, when administered in proximity in time to the beginning of a meal, exhibits a ratio of glucose exposure, $AUC_{GLU}$ in min*mg/dL, to insulin exposure, $AUC_{INS}$ in μU/mL, that is less than the ratio for subcutaneous administration of a dose of insulin providing substantially similar insulin exposure.

In another embodiment of the present invention, a pharmaceutical composition is provided comprising insulin in a rapidly absorbable form suitable for administration to an ambulatory patient which, when administered in proximity in time to the beginning of a meal, exhibits a ratio of glucose exposure, $AUC_{GLU}$ in min*mg/dL, to insulin exposure, $AUC_{INS}$ in μU/mL, that is less than 1. In an embodiment of the present invention the pharmaceutical composition is suitable for pulmonary delivery.

In an embodiment of the present invention, a pharmaceutical composition is provided wherein the insulin is complexed with a diketopiperazine microparticle, preferably fumaryl diketopiperazine.

In another embodiment of the present invention, a method of improving the reproducibility of insulin therapy is provided comprising administering the pharmaceutical composition in proximity in time to beginning meals.

In one embodiment of the present invention, a method of treating an insulin-related disorder is provided comprising administering to a patient having an insulin-related disorder an exogenously-administered composition such that the exogenously-administered insulin composition mimics first-phase insulin kinetics, and wherein the exogenously-administered insulin composition is not administered intravenously.

In another embodiment of the method of treating an insulin-related disorder of the present invention, the exogenously-administered insulin composition comprises a complex between a diketopiperazine and human insulin. In another embodiment, the diketopiperazine is fumaryl diketopiperazine. In yet another embodiment, the exogenously-administered insulin composition is inhaled.

In yet another embodiment of the method of treating an insulin-related disorder of the present invention, the insulin-related disorder is diabetes mellitus, such as type 1 or type 2 diabetes mellitus.

In one embodiment of the present invention, a method of maintaining blood glucose levels in a patient with an insulin-related disorder in a normal range is provided comprising providing an exogenously-administered insulin composition wherein first-phase insulin pharmacokinetics are obtained within about 30 minutes of administration, alternatively within about 15 minutes of administration and wherein the exogenously-administered insulin composition is not administered intravenously.

In another embodiment of the method of maintaining blood glucose levels of the present invention, the exogenously-administered insulin composition comprises a complex between a diketopiperazine and human insulin. In another embodiment, the diketopiperazine is fumaryl diketopiperazine.

In another embodiment of the method of maintaining blood glucose levels of the present invention, the exogenously administered insulin composition is a non-naturally occurring form of insulin.

In one embodiment of the present invention, a method of restoring normal insulin kinetics in a patient in need thereof is provided comprising administering to a patient having an insulin-related disorder an inhaled insulin composition such that the inhaled insulin composition mimics first-phase insulin kinetics. In another embodiment, the insulin-related disorder is diabetes mellitus. In yet another embodiment, the method further comprises administering a long-acting basal insulin.

EXAMPLES

Example 1

Insulin Concentration at Different Dose Levels Indicates Linear Absorption

Various dosages of TECHNOSPHERE®/Insulin (TI, MannKind Corporation) were administered to human subjects and insulin concentration in the blood was measured (FIG. 7A). Insulin absorption, as AUC, was linear with dosage at least up to 100 U TI (FIG. 7B).

Example 2

Mimicry of the Early Phase Insulin Response in Humans with Rapidly Bioavailable Inhaled Insulin Accelerates Post Prandial Glucose Disposal Compared to Insulin with Slower Bioavailability The relationship between time, insulin concentration and glucose elimination rate in a group of 12 subjects with type 2 diabetes, during an isoglycemic clamp was studied. Each subject received 24 IU subcutaneous soluble human insulin (ACTRAPID®, Novo Nordisk) or 48 U TECHNOSPHERE®/Insulin (TI) on separate study days in a cross-over design.

Figure 8:
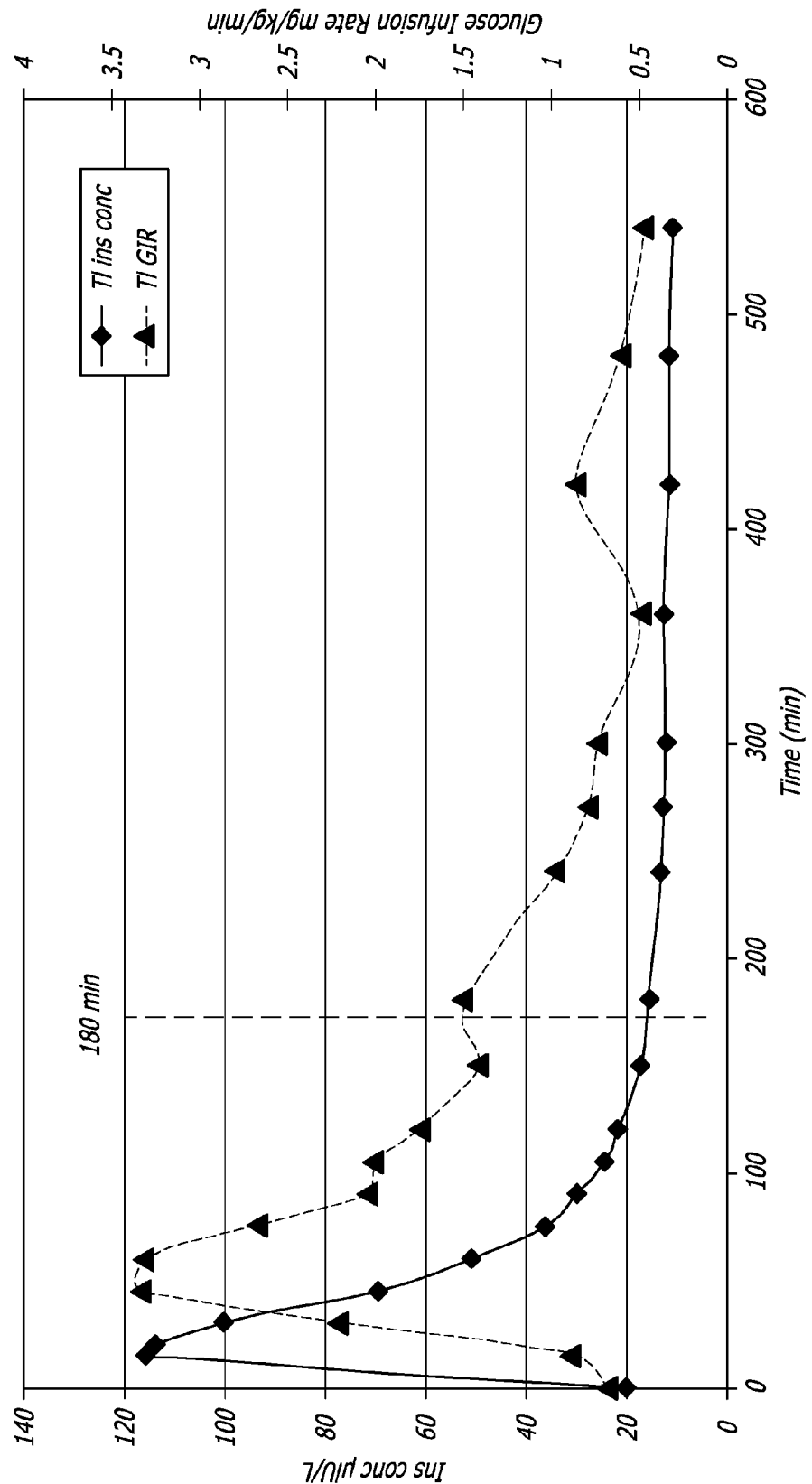
FIG. 8 depicts a comparison of insulin concentration and glucose elimination rate over time in individuals with type 2 diabetes mellitus after administration of 48 U of TI according to the teachings of the present invention.

The glucose elimination rate (GIR) was determined by the amount of glucose infusion required to maintain stable blood glucose of 120 mg/dL during the 540 min study period (FIG. 4). Forty-eight units TI provided a mean maximum concentration of insulin ($C_{max}$) of 114.8±44.1 (mean±SD) mIU/L and had a median time to maximum concentration ($T_{max}$) of 15 min, whereas 24 IU subcutaneous insulin (SC) had a $C_{max}$ of 63±10.1 mIU/L with a $T_{max}$ of 150 min. TECHNOSPHERE®/Insulin reached maximal GIR values, 3.33±1.35 mg/min/kg, at 45 min, while at that timepoint, SC was only 1.58±1.03 and did not reach maximal value, 3.38±1.45 before 255 min, despite almost constant insulin concentrations. The data for GIR and insulin concentration for TI are also plotted individually versus time in FIG. 8. Once maximal insulin effect was reached, the concentration-effect relationship was the same for TI and SC (FIG. 4). At 180 min, glucose disposal was 326±119 mg/kg or 61% of total for TI and 330±153 mg/kg (27% of total) for SC.

A fast, sharp increase in insulin concentration, similar to the early phase insulin response, provided maximal glucose elimination rate. Forty-eight units TI achieved maximal effect within 45 min, whereas it took 270 min for 24 IU SC to reach similar effect. This phenomenon is not caused by differences in the dose-effect relationship for the two insulin types, but reflects a difference in response when the increment in insulin concentration is more modest over time as opposed to the more rapid bioavailable insulin provided by TECHNOSPHERE®/Insulin. This can have consequences for postprandial glucose control.

Figure 14A:
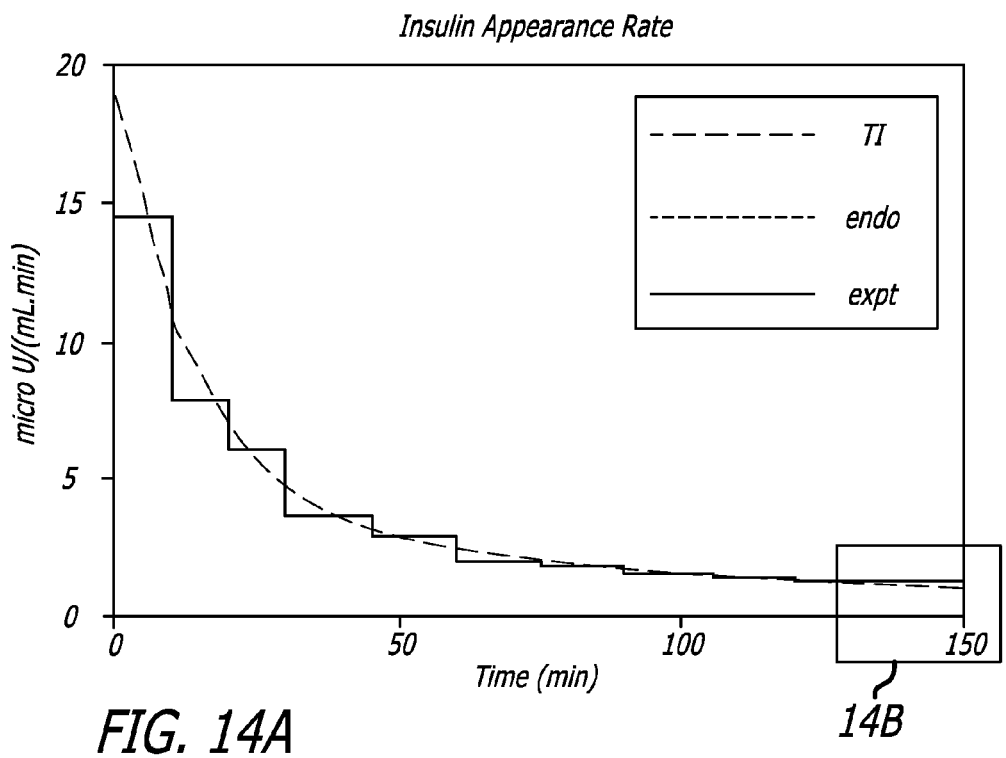
FIGS. 14A-B depict the insulin appearance rate over time for TI and endogenous insulin after administration of TI in patients with type 2 diabetes according to the teachings of the present invention
Figure 14B:
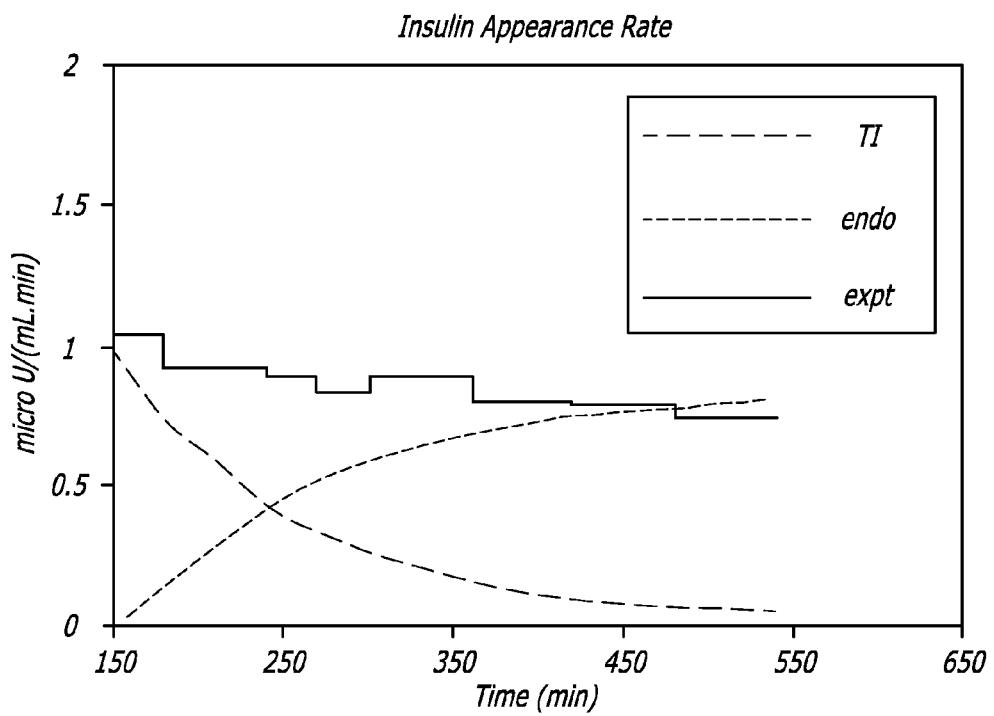

Additionally, three hours after dosing, 48 U TI and 24 IU SC had exerted the same glucose lowering effect. However, less than one-third of the total glucose lowering effect for the SC dose had been obtained. The percent of total glucose lowering activity provided within 180 minutes after a meal was 74% for TI and 29% for SC insulin (FIG. 5). If the prandial insulin dose is titrated towards a goal of normoglycemia at three hours after a meal, the large remaining glucose lowering effect of SC insulin may increase the risk of late post-prandial hypoglycemia, as compared to TI. In addition to confining the bulk of glucose lowering activity to a time period more similar to the glucose load created by a meal, the kinetics exhibited by TI also allowed for the reassertion of endogenous insulin secretion sooner, that is glycemic control is returned to homeostatic mechanisms. At late time points (>150 minutes), the fall in insulin concentration lags behind what would have been expected based on the decay rate seen at earlier time points. This can be understood as the superimposition of falling exogenous insulin (from TI) and rising endogenous insulin (FIG. 14).

Figure 16:
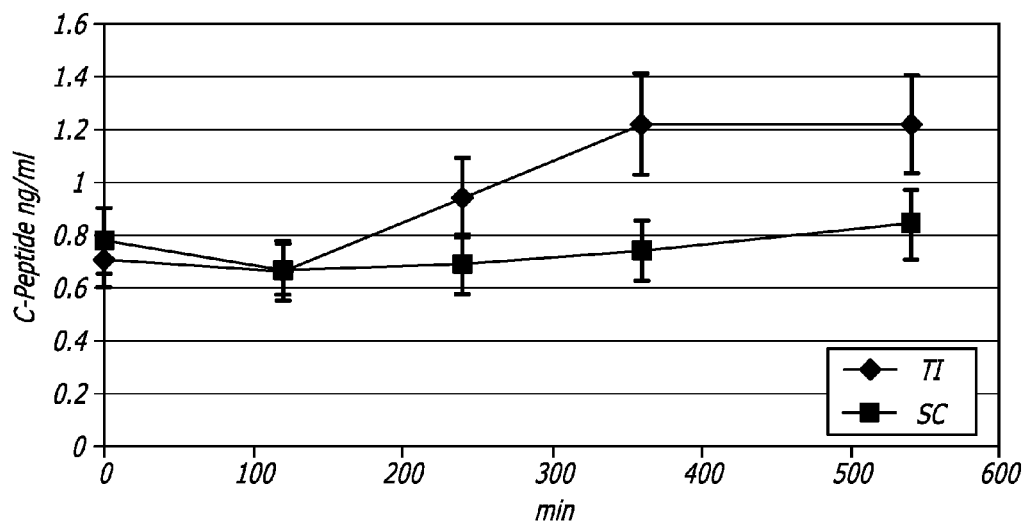
FIG. 16 depicts the levels of C-peptide after administration of TI or SC insulin in individuals with type 2 diabetes mellitus according to the teachings of the present invention.

Endogenous insulin secretion should be accompanied by the production of C-peptide. Mean serum C-peptide concentrations over time for inhaled TI and injectable SC regular insulin are presented in FIG. 16. C-peptide concentrations were essentially unchanged during SC treatment but rose with TI treatment with a timing consistent with the model depicted in FIG. 14.

One of the most important aims of drug therapy in patients with type 2 diabetes is to restore or to replace the first phase of the meal-related insulin response which is lost early in the course of type 2 diabetes mellitus. The rapid onset and short duration of action of inhaled TI should make it suitable for replacement of prandial insulin secretion in patients with diabetes mellitus.

Example 3

A Fast Insulin Spike does not Increase Risk of Hypoglycemia

Figure 15:
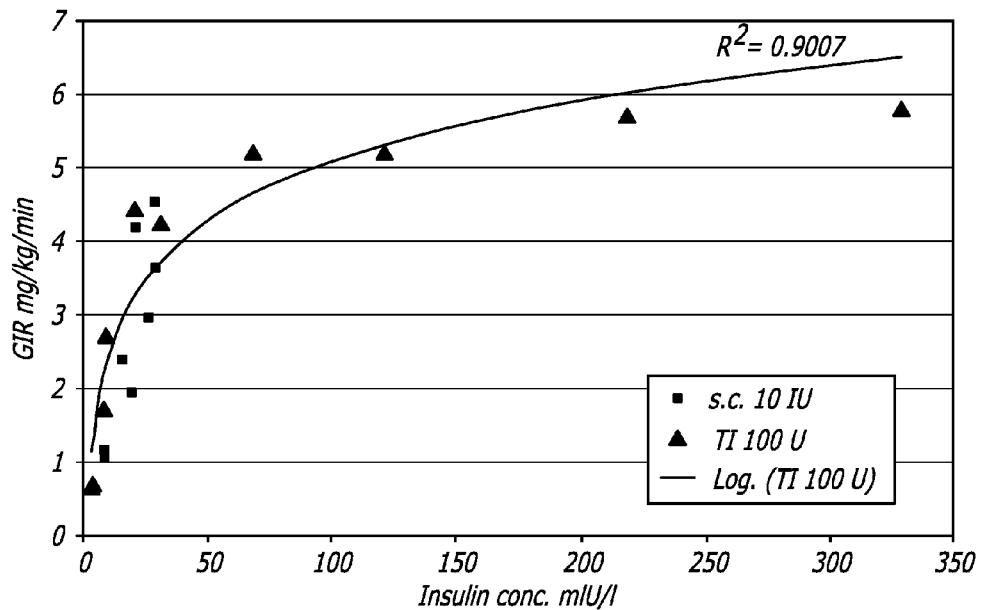
FIG. 15 depicts the relationship between insulin concentration and glucose elimination rate in individuals with type 2 diabetes mellitus after administration of intravenous (IV, 5 IU), SC (10 IU) or inhaled (TI, 100 U) insulin according to the teachings of the present invention.

It might be feared that the large concentrations of insulin, especially combined with their potentiation effect, would drive glucose elimination rates so high that they would pose a danger of inducing hypoglycemia. However this is not the case. Healthy human subjects under a euglycemic clamp were given intravenous, subcutaneous, or pulmonary insulin and the GIR was plotted against blood insulin concentration starting 20 minutes after administration. In normal subjects GIR hysteresis in response to insulin is much less pronounced than that for type 2 diabetics as disclosed in Example 1 above. Thus for normal subjects, 20 minutes after insulin administration and onward the relation between GIR and insulin concentration approximates a true mathematical function. It was observed that while at lower insulin concentrations the function appeared linear, consideration of higher concentrations showed that the relationship was actually logarithmic; as insulin concentration rose, ever smaller increases in GIR were obtained (FIG. 15). Thus glucose elimination did not reach catastrophically high rates and appeared unable to do so.

Example 4

The Variability and Time-Action Profile of Inhaled TECHNOSPHERE®/Insulin Compares Favorably to that of Subcutaneous Human Regular Insulin Timing and reproducibility and of insulin's metabolic effect is critical to achieve near-normal glucose control and to enable patients and doctors to make appropriate dose adjustments. The time-action profiles and the intra-subject variability in insulin absorption and insulin effect between repeated doses of 48 U inhaled TECHNOSPHERE®/Insulin (TI) and 24 IU subcutaneous injected human regular insulin (SC) was compared.

TECHNOSPHERE®/Insulin and SC were given on three separate occasions each on separate study days in a randomized sequence in 12 insulin-treated subjects with type 2 diabetes (10 males, 2 females, age 56 (range 40-65) years, diabetes duration 14.4 (3-29) years, HbA1c 6.9±0.9% (mean±SD), all normal lung function (FVC, FEV1 and VC=80% of predicted normal)). Using a euglycemic glucose clamp (clamp level 120 mg/dL), pharmacokinetic (PK) and pharmacodynamic (PD) time-action profiles were measured over 540 min following each form of insulin administration. Variability of absorption and effect, expressed as CV % of $AUC_{0-t}$, was determined at 120, 180 and 540 min after dosing.

Figure 6A:
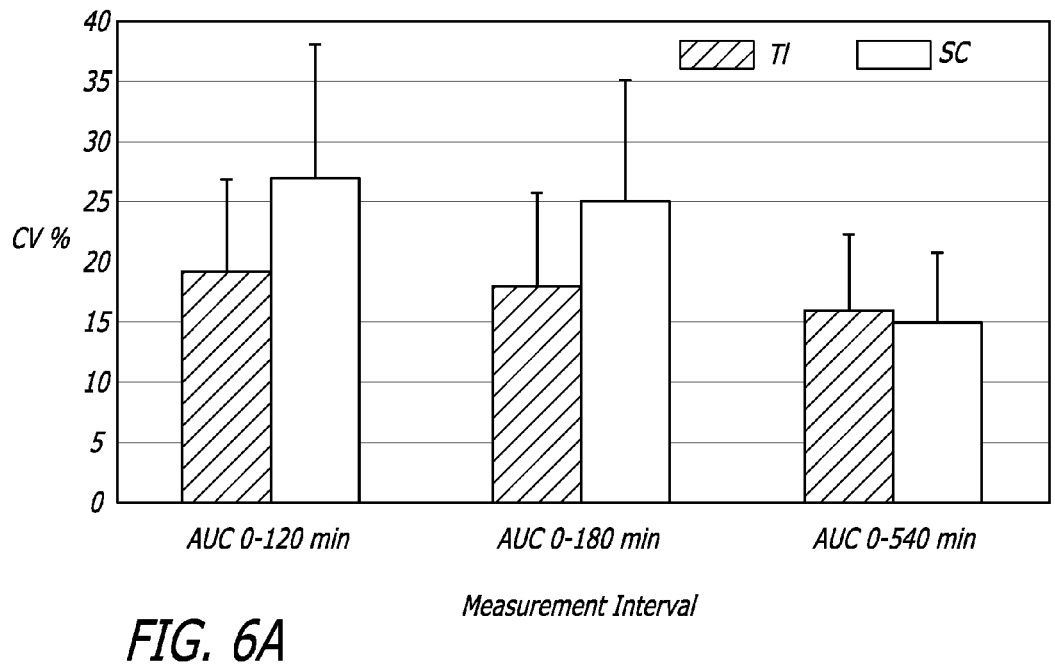
FIGS. 6A-B depict comparisons in intra-patient variability in GIR (FIG. 6A) and insulin concentration (FIG. 6B) in individuals with type 2 diabetes mellitus at various time points for subcutaneous (SC) and pulmonary (TI) insulin according to the teachings of the present invention.
Figure 6B:
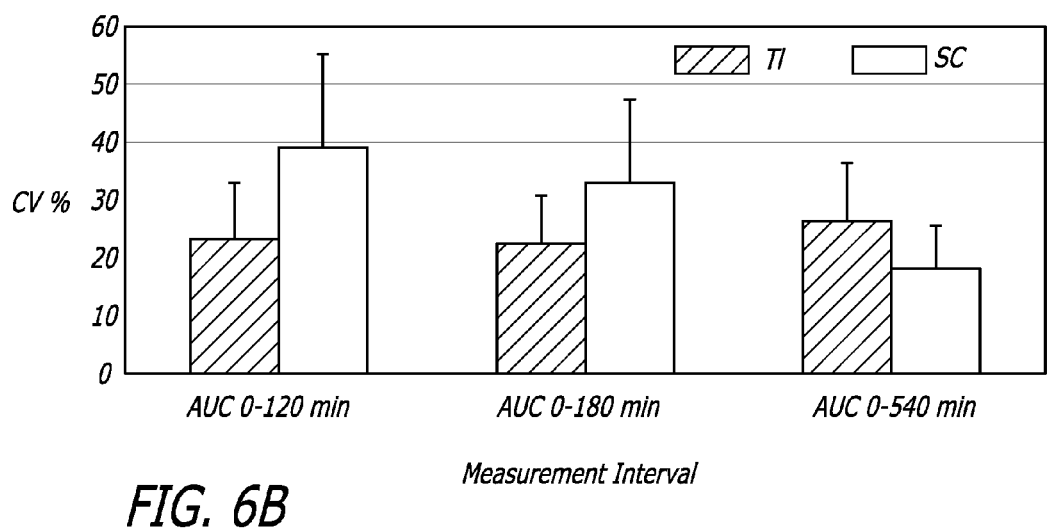

TECHNOSPHERE®/Insulin showed a more rapid onset of action (INS-$T_{max}$ 17±6 vs. 135±68 min, TI vs. SC, p<0.0001) and higher peak insulin concentrations (INS-$C_{max}$) than SC (Table 1). TECHNOSPHERE®/Insulin reached maximal glucose infusion rate (GIR) values already at 79±47 min, while the maximum effect of the SC dose occurred at 293±83 min (p<0.00001). The AUCs for both INS and GIR curves were higher for TI compared to SC in the first two and three hours after administration (Table 1). The variability in both insulin concentrations and insulin action was lower for TI compared to SC in the first three hours after administration. Specifically, for TI the variability in insulin effect (GIR) was 23%, 22% and 26% at 120, 180 and 540 min respectively, as compared to 39%, 33% and 18% for SC (FIG. 6A). The variability in insulin concentrations (FIG. 6B) followed a similar pattern (19%, 18% and 16% for TI and 27%, 25% and 15% for SC)[[.]]. At 270 min, GIR for TI had returned to baseline, and the variability in measured plasma insulin at 540 min was comparable to the variation of SC (CV %: GIR-$AUC_{0-540}$ min 26% vs. 18% (TI vs. SC); INS-$AUC_{0-540}$ min 16% vs. 15%).

TECHNOSPHERE®/Insulin showed a more rapid onset and a shorter duration of action than subcutaneous regular human insulin which can make it suitable for replacement of prandial insulin secretion in patients with type 2 diabetes. In particular, TI can provide a lower risk of late postprandial hypoglycemia as, in contrast to SC, most of its glucose lowering effect occurred before the three hour point. Furthermore, the intra-patient variability of repeated inhalations of TI was superior to SC insulin during the first three hours after dosing which can facilitate dose titration.

TABLE 1

Pharmacokinetic Parameters after Pulmonary Administration of TI Inhaled

| | TECHNOSPHERE ® Insulin | | SC Human Regular Insulin | |
|---|---|---|---|---|
| | mean ± SD | CV (%) [95% CI] | mean ± SD | CV (%) [95% CI] |
| Pharmacodynamic (PD) Parameters, based on glucose infusion rates (GIR) | | | | |
| GIR-AUC$_{0-2h}$ (mg/kg) | 265 ± 83 (44% of total) | 23.4 [13.9-33.0] | 211 ± 84 (16% of total) | 39.2 [23.2-55.2] |
| GIR-AUC$_{0-3h}$ (mg/kg) | 355 ± 119 (59% of total) | 21.7 [12.9-30.6] | 363 ± 153 (27% of total) | 33.4 [19.8-47.1] |
| GIR$_{max}$ (mg/kg/min) | 4.5 ± 1.0$^+$ | 22.0 [13.0-30.9] | 5.5 ± 1.4 | 17.3 [10.3-24.4] |
| Pharmacokinetic (PK) Parameters, based on plasma insulin (INS) concentrations | | | | |
| INS-AUC$_{0-2h}$ (µU/ml) | 6965 ± 2233* (56% of total) | 19.1 [11.3-26.9] | 5509 ± 1094 (24% of total) | 27.1 [16.1-38.2] |
| INS-AUC$_{0-3h}$ (µU/ml) | 8030 ± 2561 (64% of total) | 18.2 [10.8-24.6] | 8672 ± 1442 (38% of total) | 25.0 [14.8-35.2] |
| INS-C$_{max}$ (µU/ml) | 124 ± 44$^+$ | 20.4 [12.1-28.8] | 63 ± 10 | 29.2 [17.3-41.2] |

CI: Confidence Interval
*p < 0.05 vs. SC, $^+$p < 0.0005 vs. SC (ANOVA, Mixed Effects Models)

Example 5

A Randomized, Double-Blind, Placebo Controlled Study of the Efficacy and Safety of Inhaled TECHNOSPHERE®/Insulin in Patients with Type 2 Diabetes TECHNOSPHERE® dry powder pulmonary insulin delivered via a small inhaler (MEDTONE®, Mannkind Corp., Valencia Calif.) has a bioavailability that mimics normal, meal-related, first- or early-phase insulin release. This multicenter, randomized, double-blind, placebo-controlled study was conducted in type 2 diabetes mellitus patients inadequately controlled on diet or oral agent therapy (HbA1c>6.5% to 10.5%). A total of 123 patients were enrolled and 119, the intention-to-treat population (ITT), were randomized in a 1:1 ratio to receive prandial inhaled TECHNOSPHERE®/Insulin (TI) from unit dose cartridges containing between 6 to 48 units of human insulin (rDNA origin) or inhaled TECHNOSPHERE®/placebo for 12 weeks. TI was inhaled at the time of the first mouthful of food at each main or substantive meal of the day, amounting to 3 or 4 administrations per day throughout the 12 week trial. Subjects continued whatever oral diabetes drugs they were using prior to entering the study. Differences in HbA1c from the first and final treatment visits, and between the first and two intermediate visits, were determined, as was the change in blood glucose, as AUC at various time points, and C$_{max}$ and T$_{max}$, after a meal challenge.

Patients were given a standardized meal several times during the study and their blood glucose levels measured. The study drug was administered at the study site in conjunction with a standardized breakfast that was prepared at the site. Fasting plasma glucose was measured immediately before the meal. Spirometry was performed before the subject took the first dose of study drug. Subjects then inhaled the study drug and, within 60 seconds, performed a single spirometry test procedure. Within 90 seconds of the study drug inhalation, and after the spirometry test, the subject began eating the test meal. Once the meal was completed, the plasma glucose values and glucose meter readings were obtained at immediately before and at 30, 60 and 120 minutes after beginning the meal.

Figure 11:
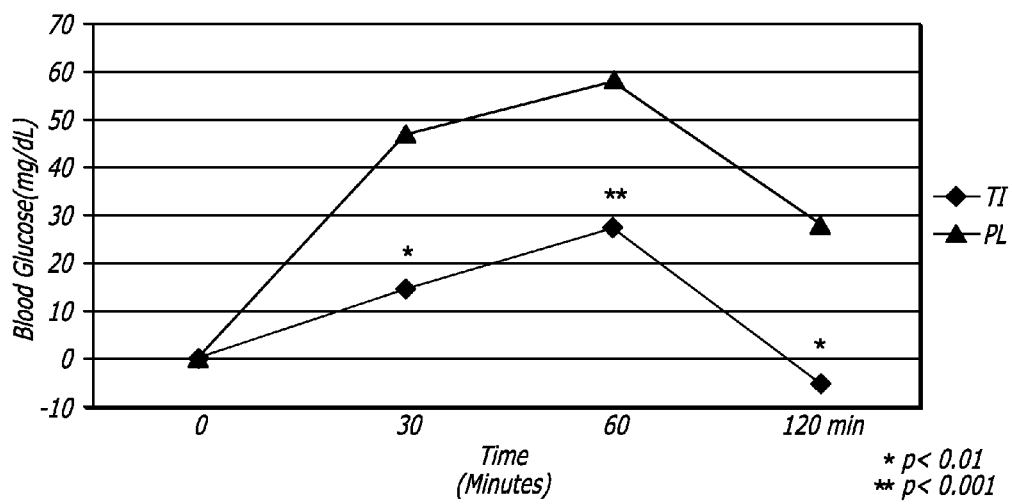
FIG. 11 depicts maintenance of the effects of inhaled insulin on postprandial glucose levels after three months of insulin therapy in individuals with type 2 diabetes mellitus with TI or placebo (PL) according to the teachings of the present invention.
Figure 12A:
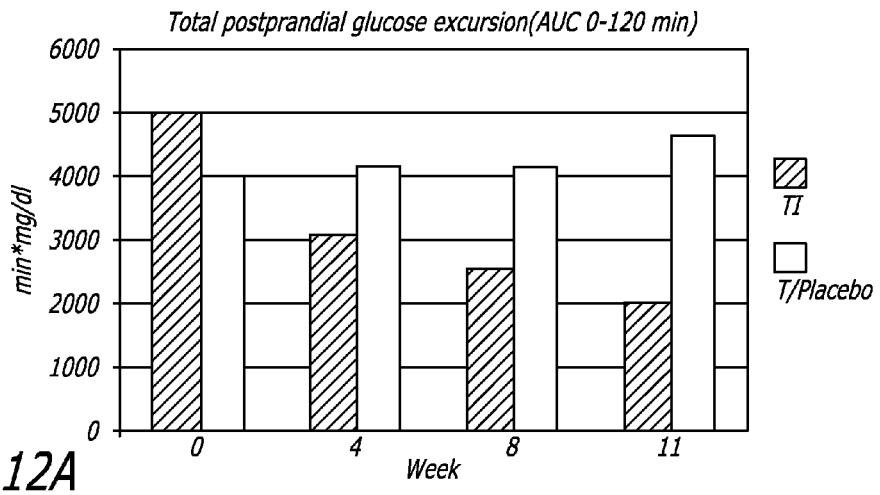
FIGS. 12A-B depict total (FIG. 12A) and maximum (FIG. 12B) postprandial glucose excursion in individuals with type 2 diabetes mellitus after administration of TI or PL according to the teachings of the present invention.
Figure 12B:
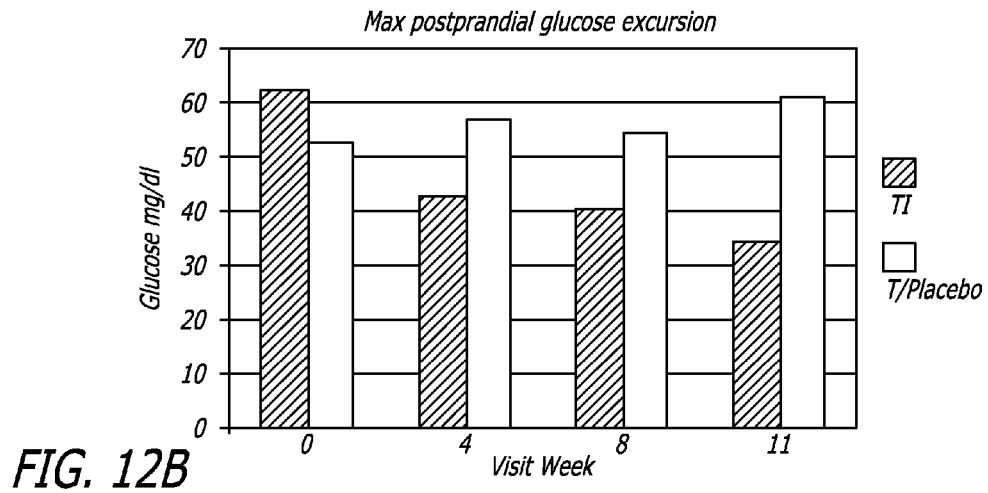
Figure 13:
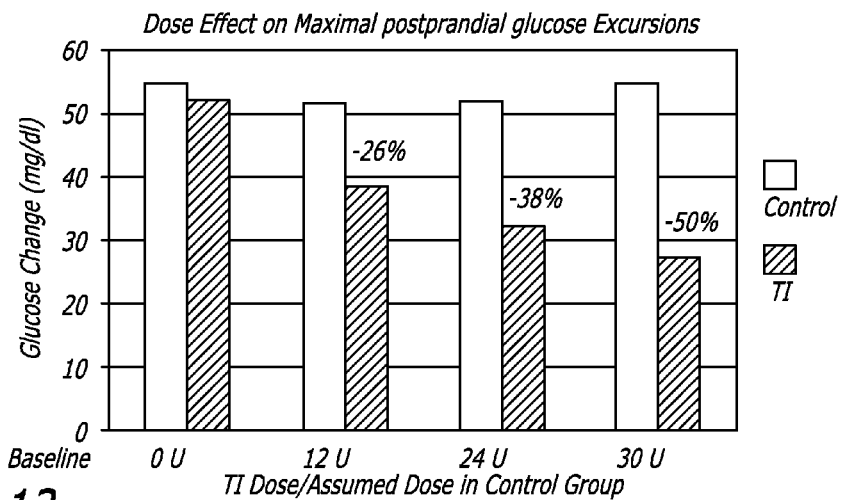
FIG. 13 depicts the dose effect on maximal postprandial glucose excursions after administration of TI compared to the assumed dose in a control group (Control) in individuals with type 2 diabetes mellitus according to the teachings of the present invention.

For patients receiving either TI or placebo, blood glucose rose after meal challenge, but significantly less for the TI group and returned to baseline sooner (FIG. 11). Thus total glucose exposure, expressed as AUC$_{0-120}$, (FIG. 12A) and maximal glucose excursion (C$_{max}$; FIG. 12B) were reduced. FIG. 13 shows the observed difference in maximal glucose excursions between the patients receiving different dosages of TI versus those in the control arm. Note that at a dose of 30 U the maximal glucose excursions for the TI patients were 50% of the level for the patients in the control group. Also note that the average glucose excursion was about 28 mg/dL vs. 50 mg/dL when the TI patients entered the study. An excursion of only 28 mg/dL is within the range that is a goal of clinical treatment.

Glycosylated hemoglobin A1c (HbA1c) results were analyzed by a pre-determined statistical analysis plan for the Primary Efficacy Population (PEP, defined prior to un-blinding as those who adhered to study requirements including minimal dosing and no adjustments of concomitant diabetes drugs), for a PEP Sub-group A (those with baseline HbA1c of 6.6 to 7.9%), for a PEP Sub-group B (those with baseline HbA1c of 8.0 to 10.5%), as well as for the ITT. These results are summarized in Table 2, and for PEP Sub-group B in FIG. 17. In this "individualized dose" study, the mean dose of TI used before each meal in the active treatment group was approximately 30 units, with 28 units used in PEP Sub-group A and 33.5 units used in PEP Sub-group B.

TABLE 2

HbA1c Pharmacokinetics

| | TECHNOSPHERE ®/ Placebo | TECHNOSPHERE ®/ Insulin |
|---|---|---|
| PEP n = 90 | n = 42 | n = 48 |
| Mean HbA1c Baseline (%) | 7.75 | 7.74 |
| Mean Δ from baseline | −0.32 (p = 0.0028) | −0.76 (p < 0.0001) |
| Comparison to Placebo | | p = 0.0019 |
| PEP Sub-group B n = 35 | n = 18 | n = 17 |
| Mean HbA1c Baseline (%) | 8.52 | 8.72 |
| Mean Δ from baseline | −0.51 (p = 0.0094) | −1.37 (p < 0.0001) |
| Comparison to Placebo | | p = 0.0007 |
| PEP Sub-group A n = 55 | n = 24 | n = 31 |
| Mean HbA1c Baseline (%) | 7.16 | 7.19 |
| Mean Δ from baseline | −0.18 (p = 0.1292) | −0.43 (p = 0.0001) |
| Comparison to Placebo | | p < 0.05 |
| ITT (LOCF) n = 119 | n = 61 | n = 58 |
| Mean HbA1c Baseline (%) | 7.78 | 7.87 |
| Mean Δ from Baseline (%) | −0.31 (p = 0.0020) | −0.72 (p < 0.0001) |
| Comparison to Placebo | | p = 0.0016 |

No episodes of severe hypoglycemia occurred in the TI group. There was no statistically significant difference in the rate of hypoglycemic events between those subjects receiving placebo and those receiving TI. (Table 3).

TABLE 3

Incidence of Hypoglycemia after Pulmonary Administration of TI

|  | TECHNOSPHERE ®/ Insulin | TECHNOSPHERE ®/ Placebo |
|---|---|---|
| Hypoglycemia (% of patients) | 42.6% | 35.5% |
| Hypoglycemia (events/week) | 0.16 | 0.20 |

Figure 19A:
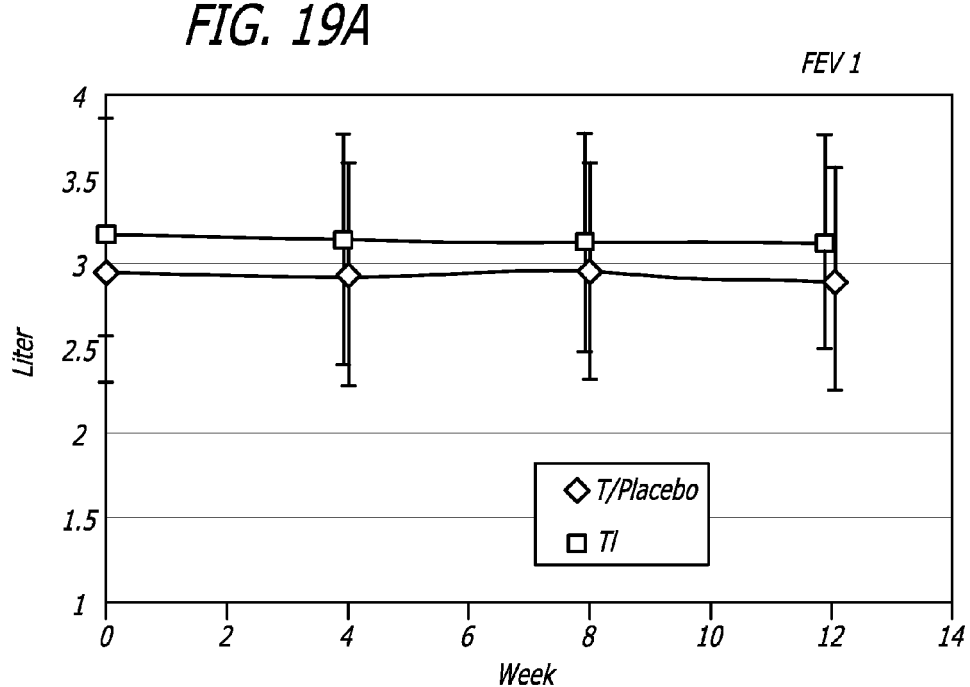
FIGS. 19A-B depict pulmonary function, expressed as forced expiratory volume in one second (FEV1, FIG. 19A)
Figure 19B:
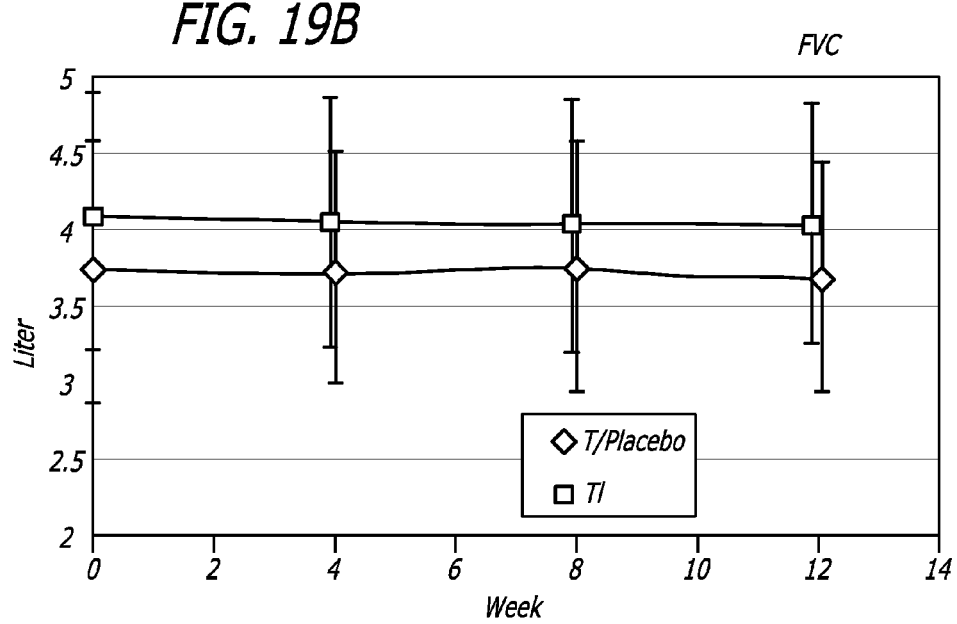

Pulmonary function tests, including DLco (diffusing capacity of the lung for carbon monoxide) (Table 4), FEV1 (forced expiratory volume in one second), and total alveolar volume (forced vital capacity, FVC) showed no significant differences between patients on TI compared to their baseline values or compared to the results of those receiving placebo (FIG. 19).

TABLE 4

Pulmonary Function After Pulmonary Administration of TI

| DLco | TECHNOSPHERE ®/Insulin | TECHNOSPHERE ®/Placebo |
|---|---|---|
| 0 weeks | 24.9 ± 4.8 | 26.5 ± 5.6 |
| 12 weeks | 25.0 ± 4.5 | 25.7 ± 5.2 |

Figure 18:
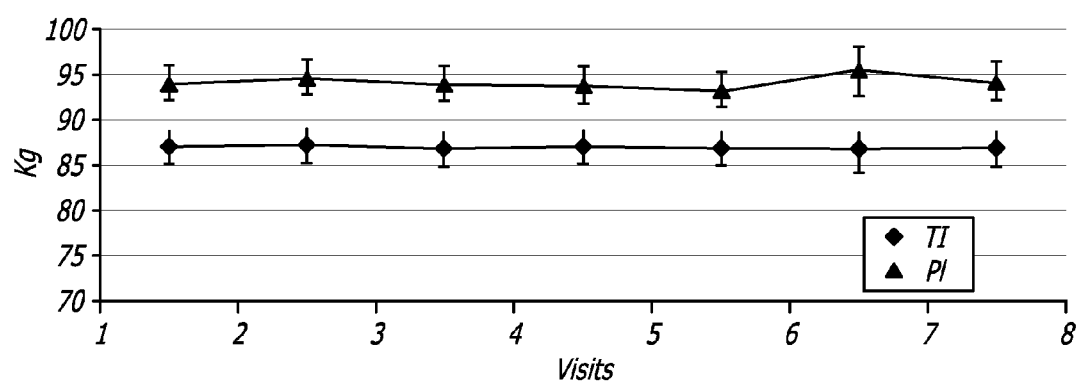
FIG. 18 depicts weight levels in individuals with type 2 diabetes mellitus administered TI or placebo (PL) according to the teachings of the present invention.

There was no evidence of induction of insulin antibodies with TI (Table 5) or of weight gain (FIG. 18) during the 12 week period of exposure.

TABLE 5

Incidence of Antibodies to Insulin after Pulmonary Administration of TI

|  | TECHNOSPHERE ®/ Insulin | TECHNOSPHERE ®/ Placebo |
|---|---|---|
| Negative at Visit 1/ Negative at Visit 9 | 38 | 34 |
| Negative at Visit 1/ Positive at Visit 9 | 2 | 3 |
| Positive at Visit 1/ Positive at Visit 9 | 8 | 10 |
| Positive at Visit 1/ Negative at Visit 9 | 2 | 4 |

In conclusion, this study has demonstrated that TECHNOSPHERE® pulmonary insulin, in replication of the kinetics of the early phase of insulin release, when used in patients with inadequate glycemic control previously on only diet and exercise alone or on oral agent therapy, safely and significantly improved glycemic control with no significantly increased incidence of hypoglycemia, no induction of insulin antibodies, no tendency toward weight gain, and no evidence of overall impact on pulmonary function.

Example 6

FDKP/Insulin Provides Glycemic Control when Administered from 10 Minutes Before to 30 Minutes After the Beginning of a Meal A clinical trial was conducted to evaluate the effect of the timing of pulmonary administration of an FDKP-insulin complex as a dry powder (FDKP/Insulin; also referred to as TECHNOSPHERE®/Insulin, TI). Subjects were type 1 diabetics who were not receiving any drug, other than insulin, for treatment of their diabetes, nor any other drug affecting carbohydrate metabolism. The trial was a prospective, single-center, randomized, crossover, open-label study. At each of 8 treatment visits, human subjects inhaled a single individualized dose 10 min before (B10), immediately before (C0), 15 min after (A15), or 30 min after (A30) eating an isocaloric (I; approximately 500 kcal) or hypercaloric (H; approximately 720 kcal) meal. Each subject received each of the eight possible timings of administration/meal combinations (i.e., B10I, B10H, C0I, C0H, A15I, A15H, A30I, and A30H) on separate occasions and in random order, with 1 to 14 days elapsing between treatment visits (see FIG. 20). Blood samples taken before and after inhalation of the TI and meal consumption were used to determine pharmacokinetic parameters for glucose and insulin.

The dose of TI was individualized for each subject. The individualized dose was based on the carbohydrate content of the meal to be consumed during the treatment visit, a correction factor for TI bioavailability, and the subject individual "insulin factor" (Fi), which was determined during a preliminary visit before the first treatment visit. The method of dose individualization was calculated at each treatment visit according to the following formula:

$$IUdose = (BE * Fi)/0.30$$

where:
IUdose was the number of IU of TI to be administered
BE (Brot-Einheit, bread unit) was 1/10 of the carbohydrate content (in grams) of the meal to be consumed (5 for the isocaloric and 8.5 for the hypercaloric meals, respectively)
Fi was the individual insulin factor, equivalent to the units of insulin required to cover one BE.
0.30 was the correction factor for TI bioavailability.

After calculation, the dose of TI was rounded to the nearest dose that could be administered using multiples of the TI cartridges, which contained 6 U, 12 U, or 24 U insulin.

During treatment visits, insulin was infused intravenously at a rate of 1 IU/hour and glucose was infused at a rate adjusted to achieve a stable capillary blood glucose concentration within the range of 80 to 140 mg/dL before meal consumption and/or TI inhalation. This infusion was continued without adjustment during the study. Venous blood samples were collected at varying intervals, starting at 45 min prior to meal consumption and continuing until four hours after consumption. The samples were used for determination of blood (serum) glucose and serum insulin concentrations.

The primary efficacy variable was blood glucose concentration. As well as providing a profile of the blood glucose concentration before and after TI and meal administration, the blood glucose concentration values were used to calculate the following pharmacokinetic parameters to describe total glucose excursion:

Maximal ($C_{max}$) and minimal ($C_{min}$) blood glucose concentrations after the start of meal consumption, corrected for baseline values.
Minimal ($C_{min}$) blood glucose concentrations after TI inhalation, corrected for baseline values.
Time to $C_{max}$ ($T_{max}$), time to $C_{min}$ ($T_{min}$), and time to last glucose excursion above baseline levels after start of meal ($T_x$).
Area under the blood glucose concentration curve (AUC) was calculated using trapezoidal method for three separate time periods:
AUC: from 10 min before to 240 min after start of meal
AUC1: from 10 min before to $T_x$, and
AUC2: from $T_x$ to 240 min after start of meal.

Blood glucose concentration at 1 hour (BG1) and 2 hours (BG2) after start of meal.

To ensure baselines were comparable between treatments, blood glucose and serum insulin baselines were computed based on the average of the −45, −30 and −20 min pre-meal measurements.

The secondary efficacy variable was serum insulin concentration. Insulin absorption was assumed to be independent of the time of dose relative to meals. The pharmacokinetic profile for insulin was determined based on serum insulin values normalized for dose and using dosing time as T=0 for all data sets. Mean $C_{max}$ (peak insulin concentration), AUC (area under the insulin concentration time curve), Tmax (time from dosing to peak concentration), time from dosing to reach 50% of $C_{max}$ (early $T_{50\%}$), and time from $T_{max}$ to 50% decline in $C_{max}$ (late $T_{50\%}$) were calculated. Following normalization (to a hypothetical 100 IU) for individual dose, intra- and inter-individual variation was determined as the CV % for the mean of individual $C_{max}$ and AUC.

line) and initial period of the area under the glucose concentration curve (AUC1), the greatest reduction in blood glucose occurred when TI was inhaled 10 min before subjects started eating either the isocaloric or hypercaloric meal ($C_{min}$ −21 mg/dL and −27 mg/dL, respectively; AUC1 −722 and −907 min*mg/dL, respectively) (Table 6). When TI was inhaled either 10 min before or immediately before meal consumption, blood glucose levels reached a nadir in approximately 10 to 13 min (as indicated by the median $T_{min}$), and did not rise above baseline levels until 20 to 30 min later (as indicated by the median $T_x$) (Table 6). By comparison, when TI was inhaled either 15 min or 30 min after the start of meal consumption, reductions in blood glucose were smaller ($C_{min}$ −10 to −13 mg/dL; AUC1 −141 to −176 min*mg/dL), they occurred sooner ($T_{min}$ 3 to 5 min), and they were more short-lived (approximately 6 to 7 min). The largest individual reductions in blood glucose were in subjects who inhaled TI immediately before isocaloric or hypercaloric meal consumption ($C_{min}$ −58 mg/dL and −57 mg/dL, respectively).

TABLE 6

Summary of Blood Gluclose Pharmacokinetic Parameters by Meal and Timing of Administration of TECHNOSPHERE ®/Insulin

| | Isocaloric Meal Timing of Dosing | | | | Hypercaloric Meal Timing of Dosing | | | |
|---|---|---|---|---|---|---|---|---|
| Parameter | B10 (N = 12) | C0 (N = 12) | A15 (N = 12) | A30 (N = 12) | B10 (N = 12) | C0 (N = 12) | A15 (N = 12) | A30 (N = 12) |
| $C_{min}$ (mg/dL) | −21 | −18 | −11 | −13 | −27 | −16 | −11 | −10 |
| | (14) | (15) | (14) | (7) | (8) | (14) | (7) | (7) |
| $T_{min}$ (minutes) | 10 | 13 | 5 | 5 | 13 | 10 | 5 | 3 |
| $C_{max}$ (mg/dL) | 86 | 84 | 88 | 81 | 119 | 130 | 116 | 113 |
| | (28) | (38) | (36) | (23) | (46) | (40) | (50) | (47) |
| $T_{max}$ (minutes) | 165 | 135 | 150 | 120 | 180 | 180 | 150 | 165 |
| AUC1 (min*mg/dL) | −722 | −648 | −154 | −176 | −907 | −418 | −149 | −141 |
| | (950) | (840) | (180) | (176) | (511) | (549) | (148) | (149) |
| AUC2 (min*mg/dL) | 11499 | 10989 | 13055 | 12431 | 14818 | 17395 | 16346 | 18402 |
| | (4640) | (7030) | (7616) | (4682) | (6018) | (6050) | (8326) | (8968) |
| AUC (min*mg/dL) | 10777 | 10342 | 12901 | 12255 | 13911 | 16977 | 16197 | 18261 |
| | (5339) | (7349) | (7739) | (4895) | (5840) | (6008) | (8407) | (8982) |
| BG1 (mg/dL) | 21 | 23 | 41 | 55 | 16 | 33 | 38 | 65 |
| | (32) | (25) | (32) | (23) | (23) | (21) | (31) | (24) |
| BG2 (mg/dL) | 68 | 71 | 78 | 68 | 81 | 101 | 82 | 89 |
| | (34) | (34) | (32) | (32) | (28) | (33) | (47) | (46) |
| $T_x$ (minutes) | 36.6 | 36.9 | 11.7 | 11.3 | 42.2 | 33.2 | 12.4 | 10.3 |

All values are presented as mean (SD) except for $T_{min}$, $T_{max}$ and $T_x$, which are median.

The primary efficacy variable was blood glucose concentration. The effect of timing of administration of TI on the mean (SD) baseline-corrected blood glucose concentrations before and after an isocaloric or hypercaloric meal is illustrated in FIG. 21 for the primary efficacy population. Overall, the comparative excursions in blood glucose, while greater after the hypercaloric meal than the isocaloric meal, were similar in profile for the two meal types but were dependent upon the timing of administration of TI (FIG. 21). Notably, when TI was inhaled 10 min before either meal, there was an initial decrease in blood glucose levels. After reaching a nadir about 10 min after the start of the meal, blood glucose levels rose above baseline levels approximately 30 min later. By comparison, when TI was inhaled 15 or 30 min after the start of the meal, glucose levels rose above baseline approximately 10-15 min after starting meal consumption (FIG. 21).

A comparison of pharmacokinetic parameters for blood glucose following each type of meal and for each timing of administration of TI is shown in Table 6 for the primary efficacy population. As indicated by the mean minimum blood glucose levels ($C_{min}$, expressed as change from base- Mean $C_{max}$ values (expressed as change from baseline), AUC, and AUC2 were generally comparable whether TI was given before or after a particular type of meal, though all were lower after the isocaloric meal than the hypercaloric meal (Table 6). The median time to $C_{max}$ ($T_{max}$) ranged between 120 and 165 min for the isocaloric meal and between 150 to 180 min for the hypercaloric meal. Mean blood glucose levels one hour (BG1) and two hours (BG2) after the start of meal showed no consistent relationship to time of inhalation of TI relative to either meal (Table 6), although BG1 was lowest when TI was given 10 min before the start of a meal and highest when given 30 min after the start of a meal.

The comparative effects of different times of TI inhalation on selected glucose pharmacokinetic parameters was expressed as a ratio of the value at the corresponding C0 (i.e, B10/C0, A15/C0, and A30/C0) for each meal type. These ratios, along with their 95% confidence intervals (CI), are summarized in Table 7 (primary efficacy population). These results indicated that the comparative effects of inhalation of TI immediately before meal consumption were no different than that of inhalation 10 min before meal consumption on any pharmacokinetic parameter (i.e, most B10/C0 ratios were close to 1 and the 95% CI encompassed 1 within their range). Most comparisons also yielded no differences between TI immediately before meal consumption and 15 or 30 min after.

insulin concentrations rose rapidly after TI inhalation, with the early $T_{50\%}$ ranging between three and five min and peak concentrations being observed 10 to 20 min after administration. Thereafter, serum insulin concentrations declined, with

TABLE 7

Comparison of Blood Glucose Pharmacokinetic Parameters Relative to Inhalation of TECHNOSPHERE ®/Insulin Immediately Before Meal Consumption

| | Isocaloric Meal Ratio of Test to Reference Parameter | | | Hypercaloric Meal Ratio of Test to Reference Parameter | | |
|---|---|---|---|---|---|---|
| Parameter | B10/C0 (N = 12) | A15/C0 (N = 12) | A30/C0 (N = 12) | B10/C0 (N = 12) | A15/C0 (N = 12) | A30/C0 (N = 12) |
| $C_{min}$ | 0.997 (0.470, 2.112) | 0.425 (0.210, 0.860) | 0.581 (0.302, 2.112) | 1.748 (0.470, 2.112) | 0.988 (0.470, 2.112) | 0.532 (0.470, 2.112) |
| AUC1 | 0.608 (0.133, 2.775) | 0.300 (0.067, 1.334) | 0.214 (0.053, 0.863) | 1.995 (0.803, 4.762) | 0.381 (0.154, 0.942) | 0.334 (0.137, 0.814) |
| $C_{max}$ | 1.002 (0.809, 1.240) | 1.088 (0.887, 1.334) | 0.953 (0.784, 1.157) | 0.848 (0.630, 1.143) | 0.778 (0.581, 1.041) | 0.814 (0.616, 1.076) |
| AUC2 | 1.077 (0.727, 1.596) | 1.035 (0.711, 1.506) | 1.158 (0.809, 1.657) | 0.780 (0.497, 1.226) | 0.771 (0.496, 1.198) | 0.907 (0.594, 1.385) |
| AUC | 1.105 (0.555, 2.200) | 0.722 (0.378, 1.380) | 1.245 (0.671, 2.310) | 0.727 (0.426, 1.238) | 0.753 (0.448, 1.266) | 0.910 (0.553, 1.500) |
| BG1 | 0.833 (0.451, 1.536) | 1.203 (0.656, 2.207) | 7.932 (1.143, 3.267) | 0.768 (0.491, 1.200) | 1.256 (0.810, 1.948) | 1.985 (1.379, 2.857) |
| BG2 | 0.630 (0.258, 1.536) | 1.109 (0.468, 2.627) | 0.906 (0.399, 2.058) | 0.771 (0.533, 1.114) | 0.665 (0.464, 0.953) | 0.758 (0.537, 1.069) |

All values are presented as ratio (95% confidence interval).

The secondary efficacy variable was serum insulin concentration. The profile of the mean (SD) baseline-corrected serum insulin concentrations after TI inhalation is illustrated in FIG. 22 for the primary efficacy population. There was a sharp increase in serum insulin immediately after inhalation of TI, which was independent of dosing time and meal type. Serum insulin concentrations peaked approximately 15 min after dosing and thereafter rapidly declined until 60 min after administration, after which there was a slower decline, consistent with first-order elimination.

A comparison of pharmacokinetic parameters for serum insulin for each timing of administration of TI relative to each type of meal is shown in Table 8 for the primary efficacy population. Overall, the mean $C_{max}$ (expressed as change from baseline) and AUC values for serum insulin were generally comparable, irrespective of meal type and whether TI was given before or after the meal (Table 8). Irrespective of meal type and time of dosing relative to the meal, serum the late $T_{50\%}$ ranging between 33 and 43 min, and again showed no consistent variation with time of inhalation of TI or meal type (Table 8).

TABLE 8

Summary of Serum Insulin Pharmacokinetic Parameters by Meal and Timing of Administration of TECHNOSPHERE ®/Insulin

| | Isocaloric Meal Timing of Dosing | | | | Hypercaloric Meal Timing of Dosing | | | |
|---|---|---|---|---|---|---|---|---|
| Parameter | B10 (N = 12) | C0 (N = 12) | A15 (N = 12) | A30 (N = 12) | B10 (N = 12) | C0 (N = 12) | A15 (N = 12) | A30 (N = 12) |
| $C_{max}$ (ml U/L) | 207 (145) | 179 (125) | 188 (137) | 215 (196) | 211 (138) | 137 (74) | 191 (114) | 193 (163) |
| $T_{max}$ (minutes) | 13 | 15 | 15 | 15 | 10 | 20 | 15 | 15 |
| AUC (min*ml U/L) | 12635 (15681) | 11291 (17449) | 11642 (18373) | 12649 (14838) | 10654 (7623) | 7710 (7313) | 12874 (16785) | 11662 (13210) |
| Early $T_{50\%}$ (min) | 4 | 4 | 3 | 3 | 4 | 5 | 4 | 3 |
| Late $T_{50\%}$ (min) | 40 | 40 | 33 | 43 | 43 | 42 | 39 | 39 |

All values are presented as mean (SD) except for $T_{max}$ and $T_{50\%}$, which are median.

Thus inhalation of an individualized dose of TI provides glycemic control in subjects with type 1 diabetes who consume isocaloric or hypercaloric meals. There were no differences in the pharmacokinetics of insulin based on the timing of administration relative to the meals. The administration of TI between 10 minutes prior to the time of the first bite of food and up to 30 minutes after starting a meal provides comparable glycemic control in the postprandial period.

Example 7

Bioavailability of Insulin in Diketopiperazine Pulmonary Formulation

Subjects and Methods

The study was conducted with 5 healthy male volunteers. Inclusion criteria were good health, as judged by physical examination, age: 18 to 40 years, body mass index: 18 to 26 kg/m², capability to reach peak inspiratory flow of ≧4 L/sec measured by a computer assisted spirometry and a FEV1 equal to or greater than 80% of predicted normal (FEV1=forced expiratory volume in one second). Exclusion criteria were diabetes mellitus type 1 or 2, prevalence of human insulin antibodies, history of hypersensitivity to the study medication or to drugs with similar chemical structures, history or severe or multiple allergies, treatment with any other investigational drug in the last three months before study entry, progressive fatal disease, history of drug or alcohol abuse, current drug therapy with other drugs, history significant cardiovascular, respiratory, gastrointestinal, hepatic, renal, neurological, psychiatric and/or hematological disease, ongoing respiratory tract infection or subjects defined as being smokers with evidence or history of tobacco or nicotine use.

Conduct of the Study

On the morning of the study days, the subjects came to the hospital (fasting, except for water, from midnight onward) at 7:30 a.m. The subjects were restricted from excessive physical activities and an intake of alcohol for 24 hours before each treatment day. They were randomly assigned to one of the three treatment arms. The subjects received a constant intravenous regular human insulin infusion, which was kept at 0.15 mU min⁻¹ kg⁻¹ so that serum insulin concentrations were established at 10-15 pU/mL during a period of two hours before time point 0. This low-dose infusion was continued throughout the test to suppress endogenous insulin secretion. Blood glucose was kept constant at a level of 90 mg/dL throughout the glucose clamp by a glucose controlled infusion system (BIOSTATOR™). The glucose clamp algorithm was based on the actual measured blood glucose concentration and the grade of variability in the minutes before to calculate the glucose infusion rates for keeping the blood glucose concentration constant. The insulin application (5 IU IV or 10 IU SC injection or three deep breaths inhalation per capsule (2 capsules with 50 U each) applied with a commercial inhalation device (Boehringer Ingelheim)) had to be finished immediately before time point 0. The duration of the clamp experiment was six hours from time point 0. Glucose infusion rates, blood glucose, serum-insulin and C-peptide were measured.

Bioefficacy and Bioavailability

To determine bioefficacy, the areas under the curve of the glucose infusion rates were calculated for the first three hours ($AUC_{0-180}$) after the administration and for the overall observation period of six hours after the administration ($AUC_{0-360}$) and were correlated to the amount of insulin applied. To determine bioavailability, the areas under the curve of the insulin concentrations were calculated for the first three hours ($AUC_{0-180}$) after the administration and for the overall observation period of six hours after the administration ($AUC_{0-360}$) and correlated to the amount of insulin applied.

In this clamp study, inhalation of 100 U of TECHNOSPHERE®/Insulin was well tolerated and was demonstrated to have a substantial blood glucose lowering effect with a relative bioavailability of 25.8% for the first three hours as calculated from the achieved serum insulin concentrations. TECHNOSPHERES® are microparticles (also referred to herein as microspheres) formed of diketopiperazine that self-assembles into an ordered lattice array at particular pHs, typically a low pH. They typically are produced to have a mean diameter between about 1 and about 5 μm.

Results

The pharmacokinetic results are illustrated in FIGS. 23 and 24 and in Table 9.

Efficacy Results

Inhalation of 100 U of TI revealed a peak of insulin concentration after 13 min (intravenous (IV) (5 IU): 5 min, subcutaneous (SC) (10 IU): 121 min) and a return of the insulin levels to baseline after 180 min (IV: 60 min, SC: 360 min). Biological action as measured by glucose infusion rate peaked after 39 min IV: 14 min, SC: 163 min) and lasted for more than 360 min (IV: 240 min, SC: >360 min). Absolute bioavailability (comparison to IV application) was 14.6±5.1% for the first three hours and 15.5±5.6% for the first six hours. Relative bioavailability (comparison to SC application) was 25.8±11.7% for the first three hours and 16.4±7.9% for the first six hours.

TABLE 9

Pharmacokinetic Parameters after Pulmonary Administration of TI

| | Pharmacokinetic Parameters | | |
|---|---|---|---|
| | Intravenous Administration | Inhaled TI | Subcutaneous Administration |
| Parameter Calculated on Glucose Infusion Rate | | | |
| $T_{50\%}$* | 9 min | 13 min | 60 min |
| $T_{max}$ | 14 min | 39 min | 163 min |
| $T_{-50\%}$** | 82 min | 240 min | 240 min |
| T to baseline | 240 min | >360 min | >360 min |
| Parameter Calculated on Insulin Levels | | | |
| $T_{50\%}$* | 2 min | 2.5 min | 27 min |
| $T_{max}$ | 5 min | 13 min | 121 min |
| $T_{-50\%}$** | 6 min | 35 min | 250 min |
| T to baseline | 60 min | 180 min | 360 min |

*time from baseline to half-maximal values
**time from baseline to half-maximal after passing Tmax Safety Results TECHNOSPHERE®/Insulin was shown to be safe in all patients. One patient was coughing during the inhalation without any further symptoms or signs of deterioration of the breathing system.

Conclusions

Inhalation of 100 U of TI was well tolerated and was demonstrated to have a substantial blood glucose lowering effect with a relative bioavailability of 25.8% for the first three hours as calculated from the achieved serum insulin concentrations.

Summary

In this study, the inhalation of TI was demonstrated in healthy human subjects to have a time-action profile with a rapid peak of insulin concentration ($T_{max}$: 13 min) and rapid onset of action ($T_{max}$: 39 min) and a sustained action over more than six hours. The total metabolic effect measured after inhalation of 100 U of TI was larger than after subcutaneous injection of 10 IU of insulin. The relative bioefficacy of TI was calculated to be 19.0%, while the relative bioavailability was determined to be 25.8% in the first three hours.

The data also show that inhalation of TI resulted in a much more rapid onset of action than SC insulin injection that was close to the onset of action of IV insulin injection, while duration of action of TI was comparable to that of SC insulin injection.

The drug was well tolerated and no serious adverse events were reported during the entire trial.

Example 8

Prandial TECHNOSPHERE®/Insulin Provides Significantly Better Control of Meal-Related Glucose Excursions than Prandial Subcutaneous Insulin

TECHNOSPHERE®/Insulin (TI) is a dry powder formulation of human insulin comprising insulin complexed to fumaryl diketopiperazine microparticles. TECHNOSPHERE®/Insulin was delivered by pulmonary administration with a dry powder inhaler (MEDTONE® Inhaler) accomplishing a rapid onset of action and a duration of action long enough to cover meal-related glucose absorption. The primary objective of this study was to assess safety and efficacy of pre-prandially administered TI compared to subcutaneous (SC) regular insulin on blood glucose concentration over a 7 day treatment period.

Sixteen non-smoking subjects with type 2 diabetes (age 59 (range 39-69) yrs; BMI 29.6 (23.8-34.9) kg/m$^2$; mean diabetes duration 12.3 yrs; with normal pulmonary function (forced expiratory volume in 1 sec and forced vital capacity >80% of predicted normal)) and treated with intensified insulin therapy were enrolled in this randomized, open-label, two period cross-over study. Subjects covered their prandial insulin needs either by inhaled TI or by SC insulin over a treatment period of one week, respectively, while continuing their usual basal insulin therapy. The doses of TI and SC insulin were determined during a 24 hour in-house period prior to randomization. TECHNOSPHERE®/Insulin was inhaled using a 12 U or 24 U cartridge via a hand-held inhaler. After an out-patient period during which subjects administered the assigned pre-meal therapy with either SC or TI, performed 4-point blood glucose self-measurements, and pursued their usual activities and diet for 5 to 7 days, postprandial blood glucose and serum insulin (INS) excursions were determined under in-house conditions after ingestion of a standardized breakfast (496 kcal, 55% carbohydrates) covered with either 48±9 (mean±SD) U of TI or 14±5 IU of SC insulin.

Figure 9B:
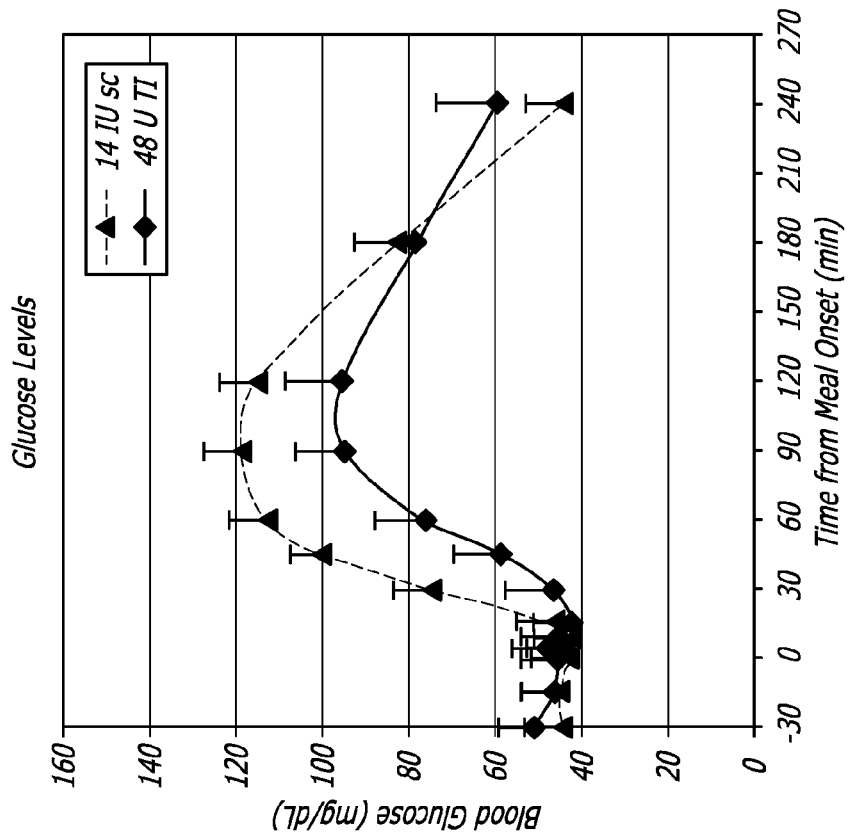
FIGS. 9A-B depict blood insulin (FIG. 9A) and glucose levels (FIG. 9B) in individuals with type 2 diabetes mellitus after administration of 14 IU SC insulin or 48 U TI according to the teachings of the present invention.

When treated with SC insulin, subjects demonstrated insulin median $T_{max}$ of 120 min with median $C_{max}$ of 54 µU/mL. In comparison, when treated with TI, subjects demonstrated insulin median $T_{max}$ of 14 min and median $C_{max}$ of 102 µU/mL (FIG. 9). Total insulin exposure for each treatment cycle was comparable for SC and for TI with mean $AUC_{INS}$ measured at 9155 and 9180 µU/mL respectively (FIG. 10). Mean excursion of glucose from baseline for SC was 85 mg/dL and $AUC_{GLU}$ was 10925 min*mg/dL. In comparison, mean excursion of glucose from baseline for TI was 59 mg/dL and $AUC_{GLU}$ was 6969 min*mg/dL (FIG. 10). Thus the ratio of glucose excursion to insulin exposure in the above units, an indication of the effectiveness of the absorbed insulin dose, was only about 0.76 versus about 1.2 for TI and SC, respectively. The data demonstrate a 31% reduction (p=0.0022) of mean glucose excursion and a 36% reduction (p=0.0073) of glucose exposure over the 240 min measured for TI relative to SC.

With comparable exposure to insulin (as measured in the plasma), to meal quantity, and to meal composition, prandial TI resulted in significantly improved control of post-prandial peak glucose and total glucose exposure compared to prandial SC. The only differences between therapies were the insulin formulations and the methods of insulin administration. TI provided insulin Tmax that mimicked first-phase insulin release kinetics and which occurred at a time when it would be expected to have an effect on hepatic glucose release. Subcutaneous insulin levels were much lower than TI during the early post-prandial period, did not exhibit a clear "peak" as did TI, and demonstrated a slow rise to maximum concentration—too late to be expected to control hepatic glucose release but sufficient to represent a risk for late post-prandial hypoglycemia.

Example 9

Markedly Reduced Postprandial Glucose Excursions Through Inhaled TECHNOSPHERE®/Insulin in Comparison to SC Injected Regular Insulin In Subjects with Type 2 Diabetes—Example 8 Data Reanalysis with ANOVA

Baseline adjusted postprandial total insulin exposure (INS-$AUC_{0-240}$ min) was comparable for TI and for SC (8187±4269 vs 8302±4025 min*µU/dL; ns) whereas baseline adjusted postprandial glucose excursion (BG-$AUC_{0-240}$ min) for TI was only about 50% of that of SC (5095±5923 min*mg/dL vs 9851±5593 min*mg/dL; p<0.008). Thus the ratio of glucose excursion to insulin exposure in the above units, an indication of the effectiveness of the absorbed insulin dose was only about 0.62 for TI versus about 1.2 for SC. In other words, unit for unit of absorbed insulin, TI was nearly twice as efficient in removing glucose from the blood. With TI, median insulin Tmax was shorter (15 vs 120 min; p<0.001) and median Cmax was higher (100 vs 54 µU/mL; p=0.001) than with SC. Accordingly, postprandial maximum adjusted blood glucose excursions were 28% lower with TI compared to SC (49 vs 82 mg/dL; p<0.003). The incidence of hypoglycemia (BG <63 mg/dL or hypoglycemic symptoms) was comparable between TI and SC (6 vs. 5 episodes) as was the number of treatment emerged (mild to moderate) adverse events (5 vs. 4 episodes). Hyperglycemia (BG >280 mg/dL) occurred more often with TI (12 vs. 4 episodes)—with two patients alone accounting for 8 episodes.

TECHNOSPHERE®/Insulin markedly improved postprandial glucose control compared to prandial SC while total serum insulin concentrations were comparable between both treatments. This was attributed to a rapid onset of action of TI in which insulin Tmax resembles first-phase insulin release kinetics. In contrast SC insulin levels were much lower than TI during the early post-prandial period and did not exhibit the clear peak observed with TI. These results support the conclusion that preprandial TI was superior to SC insulin in providing prandial insulin needs and reducing meal related blood glucose excursions.

Example 10

Multi-Center Study of Type 2 Patients Taking Prandial TI in an Ambulatory Setting

Studies of the pharmacokinetics and pharmacodynamics of administering regular human insulin by pulmonary inhalation using TECHNOSPHERE®/Insulin (TI) have indicated that maximal plasma insulin concentration can be achieved in a median of about 10 to 14 minutes after inhalation, which is ideal for replicating the first-phase insulin release. The administration of insulin with this highly reproducible kinetic profile to ambulatory patients with diabetes has not been possible with other currently available insulin systems. Studies, such as the examples above, have demonstrated a 48% reduction in post-prandial glucose excursion with TI compared to a bio-available equivalent dose of subcutaneous insulin (SC) given before meals. In another multi-center study of type 2 patients taking prandial TI in an ambulatory setting for 12 weeks, the frequency of prospectively monitored hypoglycemia was less than 10% of the frequency historically reported for SC in ambulatory use.

In a randomized, prospective double blind, placebo controlled study of the forced titration of prandial TECHNOSPHERE®/Insulin in patients with type 2 diabetes mellitus subjects received inhaled TECHNOSPHERE®/Insulin (TI), dosed prandially, in addition to basal administration of SC insulin glargine (LANTUS®; a form of long acting insulin), 227 patients were studied over 18 weeks. During the initial 4 weeks, patients were followed on their existing therapy and then removed from all oral anti-hyperglycemic therapy and placed on fixed doses of SC insulin glargine taken once daily, in a dose sufficient to replicate their documented pre-manipulation fasting plasma glucose levels and stabilized at this dose. The patients were then randomized to blinded doses of added inhaled placebo or blinded doses of inhaled TI containing 14, 28, 42 or 56 U of regular human insulin taken at the time of each main meal of the day in a forced titration scenario over 4 weeks. Specifically, the subjects, divided into five cohorts, initially received placebo (TECHNOSPHERE® microparticles without any insulin) along with the SC long acting insulin. After a week one cohort continued to receive placebo and four cohorts were switched to a TI dose of 14 U of insulin. After another week three cohorts were switched to a TI dose of 28 U, and so on until a final cohort reached a TI dose of 56 U. All cohorts then continued on the same dose for the remaining eight weeks of the trial.

HbA1c levels and meal challenges (300 min) were evaluated at the initial visit, at the start of randomized treatment and at completion. Comparisons were made between treatment groups and the placebo group. Safety was assessed by the frequency of defined hypoglycemic episodes and by the measurement of serial pulmonary function tests including $FEV_1$ and $DL_{CO}$. The addition of TI to insulin glargine produced a dose-dependent reduction in HbA1c levels. In patients treated for eight weeks at 56 units, the mean reduction was 0.79% greater than that observed in the insulin glargine/placebo group (p=0.0002). TECHNOSPHERE®/Insulin also produced a dose-dependent reduction in post-prandial glucose excursions with a maximal excursion averaging only 34 mg/dL at 56 U (p<0.0001). There were no severe hypoglycemic episodes, and the frequency of mild/moderate hypoglycemic episodes was not increased above that in subjects on insulin glargine alone. No changes were observed from baseline or between dosage groups in weight or pulmonary function. Thus inhaled TI was able to improve the glycemic control of patients with type 2 diabetes without increasing the risk of hypoglycemia.

Example 11

A 3 Month Comparison in Type 1 Diabetes of Inhaled TECHNOSPHERE®/Insulin to SC Administered Rapid-Acting Insulin Analogue as Prandial Insulin in a Basal/Prandial Regimen This study represents the first evaluation of long-term control in patients with type 1 diabetes, comparing TECHNOSPHERE®/Insulin (TI) with a rapid-acting insulin analogue (RAA, NOVOLOG®) as a comparator. Previous studies of TI has shown significantly better postprandial control than regular human insulin over 240 min in patients with type 2 diabetes.

Patients with type 1 diabetes (111 subjects, 18 to 80 years of age; HbA1c≧7.0% and ≦11.5%) were enrolled in a randomized, open label study to receive TI or RAA as meal-time insulin in addition to basal insulin (LANTUS®) for 12 weeks. Titration of both prandial and basal insulin was permitted at the physician's discretion. At baseline, week 8 and week 12, standardized meal tests were conducted to assess glucose excursions over 300 min (420 min at week 12), and HbA1c levels and lung function ($FEV_1$ and DLco) was evaluated in both groups. Lower maximum and total glucose excursions were observed in the first two hours following a standard meal in the group receiving TI insulin compared to those who were dosed with SC insulin. Over the following 3-4 hours, glycemia was maintained close to baseline levels in the TI group but fell below baseline in the patients receiving rapid acting insulin. No significant difference in HbA1c levels were observed between the two treatment groups. The reduction from baseline was 0.83 (1.11); p<001 (mean (SD) in the TI group and 0.99 (1.07); p<0.001 in the group receiving SC RAA, with no statistical difference between the groups (p=0.458). At the same time, body weight decreased by 0.41 (2.22) kg in the TI group, while it increased by 0.89 (1.92) kg in the group receiving SC insulin. The difference between groups was statistically significant (p=0.0016). An improvement in postprandial blood glucose excursions was observed in subjects receiving TI as compared to RAA. Maximal postprandial excursion at visit 10 was 0.92 mmol/L for TI vs. 3.0 mmol/L for RAA. The total postprandial glucose elevation ($AUC_{GLU}$) was 96.7 mmol/L*min for TI and 400.6 mmol/L*min for RAA. No adverse effects on pulmonary function were seen after 3 months treatment, (change in FEV1 was −0.064 l (0.189) for TI and −0.072 (0.193) for RAA (p=0.82; n.s.), and for DLco −1.62 (3.29) and −1.094 (3.08) (p=0.39; n.s.) respectively. Therefore, in a basal/prandial regimen in patients with type 1 diabetes, inhaled TI was an appropriate alternative to SC administered RAA providing similar overall glycemic control (expressed as change from baseline HbA1c) to RAA while post-prandial excursions were significantly less.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of reducing postprandial glucose excursions in a patient with an insulin-related disorder comprising:
   selecting a patient with an insulin-related disorder;
   administering a long-acting basal insulin;
   administering an insulin composition comprising fumaryl diketopiperazine in a form suitable for pulmonary administration in proximity to beginning a meal, wherein the patient's total insulin exposure (INS-AUC$_{0-y}$, $3<y<6$ hours) does not substantially exceed that produced by an appropriate subcutaneous dose of insulin; and
   reducing the postprandial glucose excursions relative to treatment with the appropriate subcutaneous dose of insulin.

2. The method of claim 1 wherein the risk of late postprandial hypoglycemia is not increased.

3. The method of claim 1, wherein the insulin is complexed with the fumaryl diketopiperazine.

4. The method of claim 1, wherein the insulin composition is administered by inhalation as a dry powder.

5. The method of claim 1, wherein the insulin composition is administered from approximately 10 minutes prior to beginning a meal to approximately 30 minutes after beginning a meal.

6. The method of claim 1, wherein the insulin-related disorder is type I diabetes mellitus.

7. The method of claim 1, wherein the insulin-related disorder is type II diabetes mellitus.

8. The method of claim 1, wherein a mean glucose excursion is at least about 25% less than for an appropriate subcutaneous dose of insulin.

9. The method of claim 1, wherein glucose excursions are measured as AUC$_{0-240}$.

10. The method of claim 1, wherein glucose excursions are measured as AUC$_{0-120}$.

11. The method of claim 1, wherein glucose excursions are measured as AUC$_{0-Tx}$.

12. The method of claim 1, wherein glucose excursions are measured as maximum glucose excursion.

13. The method of claim 12, wherein the maximum glucose excursion does not exceed a blood glucose concentration of 180 mg/dL.

14. The method of claim 12, wherein the maximum glucose excursion does not exceed a premeal baseline blood glucose concentration by more than 59 mg/dL.

15. The method of claim 12, wherein the maximum glucose excursion does not exceed the premeal baseline blood glucose concentration by more than 49 mg/dL.

16. The method of claim 12, wherein the maximum glucose excursion does not exceed the premeal baseline blood glucose concentration by more than 28 mg/dL.

* * * * *